US012774471B2

(12) United States Patent
Luesch et al.

(10) Patent No.: US 12,774,471 B2
(45) Date of Patent: Oct. 27, 2026

(54) **ENGINEERED *STREPTOMYCES ALBUS* STRAINS**

(71) Applicant: University of Florida Research Foundation, Incorporated, Gainesville, FL (US)

(72) Inventors: Hendrik Luesch, Gainesville, FL (US); Dimitrios Kallifidas, Cambridge, MA (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 1027 days.

(21) Appl. No.: 17/045,240

(22) PCT Filed: Apr. 5, 2019

(86) PCT No.: PCT/US2019/025948
§ 371 (c)(1),
(2) Date: Oct. 5, 2020

(87) PCT Pub. No.: WO2019/195655
PCT Pub. Date: Oct. 10, 2019

(65) Prior Publication Data

US 2021/0163964 A1 Jun. 3, 2021

Related U.S. Application Data

(60) Provisional application No. 62/654,145, filed on Apr. 6, 2018.

(51) Int. Cl.

| | |
|---|---|
| ***C12N 15/76*** | (2006.01) |
| ***C07K 14/36*** | (2006.01) |
| ***C12P 1/04*** | (2006.01) |
| ***C12P 7/22*** | (2006.01) |
| ***C12P 13/00*** | (2006.01) |
| ***C12P 15/00*** | (2006.01) |
| ***C12P 17/04*** | (2006.01) |
| ***C12P 17/06*** | (2006.01) |
| ***C12P 17/12*** | (2006.01) |

(52) U.S. Cl.
CPC .............. *C12N 15/76* (2013.01); *C07K 14/36* (2013.01); *C12P 1/04* (2013.01); *C12P 7/22* (2013.01); *C12P 13/00* (2013.01); *C12P 15/00* (2013.01); *C12P 17/04* (2013.01); *C12P 17/06* (2013.01); *C12P 17/12* (2013.01)

(58) Field of Classification Search
CPC .... C12P 7/22; C12P 1/04; C12P 13/00; C12P 15/00; C12P 17/04; C12P 17/06; C12P 17/12; C12N 15/76; C07K 14/36
See application file for complete search history.

(56) References Cited

U.S. PATENT DOCUMENTS

| | | | |
|---|---|---|---|
| 5,876,987 A | 3/1999 | Champness et al. | |
| 2003/0162262 A1* | 8/2003 | Ashley .................. | C12N 15/65 435/320.1 |
| 2004/0101963 A1 | 5/2004 | Bibb et al. | |
| 2006/0194285 A1 | 8/2006 | Lian et al. | |
| 2017/0081690 A1 | 3/2017 | Kahne et al. | |

FOREIGN PATENT DOCUMENTS

WO WO 2017/031399 A1 2/2017

OTHER PUBLICATIONS

Zaburannyi (BMC Genomics, vol. 2014, vol. 15, No. 97, p. 1-11, 2014) (Year: 2014).*
Borodina (The Journal of Biological Chemistry, vol. 283, No. 37, p. 25186-25199, 2008) (Year: 2008).*
Dang (J. Ind. Microbiol. Biotechnol., vol. 44, p. 259-270, 2017) (Year: 2017).*
Gao (mBio (vol. 3, No. 6, e00407-12, p. 1-12, 2012) (Year: 2012).*
Huang et al., wblA, a pleiotropic regulatory gene modulating morphogenesis and daptomycin production in Streptomyces roseosporus, Journal of Applied Microbiology, 123, 669-677: 173, Publication Date: Sep. 2017 (Year: 2017).*
Koshla et al., Arch Microbio, 2017, 199: 1175-1183, Publication Date: May 20, 2017 (Year: 2017).*
Dolya et al. Microorganisms, 2023, 11, 1176 with suppl., Publication Date: Apr. 30, 2023 (Year: 2023).*
International Search Report and Written Opinion mailed Jul. 2, 2019 in connection with International Patent Application No. PCT/US2019/025948.
International Preliminary Report on Patentability mailed Oct. 15, 2020 in connection with International Patent Application No. PCT/US2019/025948.
Kallifidas et al., Rational engineering of Streptomyces albus J1074 for the overexpression of secondary metabolite gene clusters. Microbial cell factories. Dec. 1, 2018;17(1):25. 14 pages.
Butler et al., Engineering of primary carbon metabolism for improved antibiotic production in Streptomyces lividans. Appl Environ Microbiol. Oct. 2002;68(10):4731-9. doi: 10.1128/AEM.68.10.4731-4739. 2002.

(Continued)

*Primary Examiner* — Samira J Jean-Louis
*Assistant Examiner* — Cheng Lu
(74) *Attorney, Agent, or Firm* — Wolf, Greenfield & Sacks, P.C.

(57) ABSTRACT

In some aspects, the disclosure relates to production of bacterial secondary metabolites. In some embodiments, the disclosure relates to a genetically engineered *Streptomyces* J1074 bacterium, wherein the bacterium comprises a nucleic acid having a modification to at least one global regulator gene.

5 Claims, 17 Drawing Sheets

Specification includes a Sequence Listing.

(56) References Cited

OTHER PUBLICATIONS

Nah et al., Identification and biotechnological application of novel regulatory genes involved in Streptomyces polyketide overproduction through reverse engineering strategy. Biomed Res Int. 2013:2013:549737. doi: 10.1155/2013/549737. Epub Mar. 4, 2013.

Ryu et al., Engineering of primary carbohydrate metabolism for increased production of actinorhodin in Streptomyces coelicolor. Appl Environ Microbiol. Nov. 2006;72(11):7132-9. doi: 10.1128/AEM.01308-06. Epub Sep. 1, 2006.

Zhang et al., Broad-Host-Range Expression Reveals Native and Host Regulatory Elements That Influence Heterologous Antibiotic Production in Gram-Negative Bacteria. mBio. Sep. 5, 2017;8(5):e01291-17. doi: 10.1128/mBio.01291-17.

* cited by examiner

| strain | diameter (mm) | surface (mm$^2$) |
|---|---|---|
| *S. albus* J1074 | 26.6 ± 1.5 | 559.4 ± 63.4 |
| *S. albus* Δ*pfk* | 21 ± 1.0 | 346.7 ± 32.9 |

SEQUENCE LISTING

```
<160> NUMBER OF SEQ ID NOS: 44

<210> SEQ ID NO 1
<211> LENGTH: 31
<212> TYPE: DNA
<213> ORGANISM: Artificial Sequence
<220> FEATURE:
<223> OTHER INFORMATION: Synthetic polynucleotide

<400> SEQUENCE: 1

atcgggatcc tggtcgacaa cgcgatggag g                                    31


<210> SEQ ID NO 2
<211> LENGTH: 42
<212> TYPE: DNA
<213> ORGANISM: Artificial Sequence
<220> FEATURE:
<223> OTHER INFORMATION: Synthetic polynucleotide

<400> SEQUENCE: 2

agcaggagag acagcacgat gtgaaccggc tccgcgcaca cg                        42


<210> SEQ ID NO 3
<211> LENGTH: 42
<212> TYPE: DNA
<213> ORGANISM: Artificial Sequence
<220> FEATURE:
<223> OTHER INFORMATION: Synthetic polynucleotide

<400> SEQUENCE: 3

cgtgtgcgcg gagccggttc acatcgtgct gtctctcctg ct                        42


<210> SEQ ID NO 4
<211> LENGTH: 31
<212> TYPE: DNA
<213> ORGANISM: Artificial Sequence
```

<220> FEATURE:
<223> OTHER INFORMATION: Synthetic polynucleotide

<400> SEQUENCE: 4
atcgaagctt gcccagcaga accgttccgt c 31

<210> SEQ ID NO 5
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 5
gaggtcggca tctcccgcat c 21

<210> SEQ ID NO 6
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 6
actccgacga taccggtgcg 20

<210> SEQ ID NO 7
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 7
ccatcggcac gtacctggcc 20

<210> SEQ ID NO 8
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 8
atgtccttcc tgtccccggc 20

<210> SEQ ID NO 9
<211> LENGTH: 59
<212> TYPE: DNA
<213> ORGANISM: Artificial Sequence
<220> FEATURE:
<223> OTHER INFORMATION: Synthetic polynucleotide

<400> SEQUENCE: 9
tgggggagcc tcgattcggg agaggacggc gccggtatga ttccggggat ccgtcgacc 59

<210> SEQ ID NO 10
<211> LENGTH: 58
<212> TYPE: DNA
<213> ORGANISM: Artificial Sequence
<220> FEATURE:
<223> OTHER INFORMATION: Synthetic polynucleotide

<400> SEQUENCE: 10
ggttcccgta ctcctcgctc gcccttgccg gccggtctat gtaggctgga gctgcttc 58

<210> SEQ ID NO 11
<211> LENGTH: 59
<212> TYPE: DNA
<213> ORGANISM: Artificial Sequence
<220> FEATURE:
<223> OTHER INFORMATION: Synthetic polynucleotide

<400> SEQUENCE: 11
gtaacctcgg tgtgcggttg tatgcctgct gtggattgcc gcaacgttgt tgccattgc 59

<210> SEQ ID NO 12
<211> LENGTH: 59
<212> TYPE: DNA
<213> ORGANISM: Artificial Sequence
<220> FEATURE:
<223> OTHER INFORMATION: Synthetic polynucleotide

<400> SEQUENCE: 12
agcgatgagc tcggacttcc attgttcatt ccacggacaa atccccgatc cgctccacg 59

<210> SEQ ID NO 13
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 13
gagaactcat atggacgacg ttc 23

<210> SEQ ID NO 14
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 14
cgtaagcttg gcctaggtcg cagggac 27

<210> SEQ ID NO 15
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 15
gggattccct gagcggagta c 21

<210> SEQ ID NO 16
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 16
ggtttccagg ggcccttcta g 21

<210> SEQ ID NO 17
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 17
gaaaccgctc cgtccgtccg acacc 25

<210> SEQ ID NO 18
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 18
tgcatccgca gcaccagcag g 21

<210> SEQ ID NO 19
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 19
cttaaatcct cgaaggcgac 20

<210> SEQ ID NO 20
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 20
gcgcccatca gtttggcgtg 20

<210> SEQ ID NO 21
<211> LENGTH: 14
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (4)..(9)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t

<400> SEQUENCE: 21
gtgnnnnnng ncac 14

<210> SEQ ID NO 22
<211> LENGTH: 14
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (4)..(9)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (14)..(14)

<223> OTHER INFORMATION: n is a, c, g, or t

<400> SEQUENCE: 22
gtgnnnnnng ngan 14

<210> SEQ ID NO 23
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 23
cctcgtggac accgccaccg gc 22

<210> SEQ ID NO 24
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 24
ggcggtggcc atggccacgg ag 22

<210> SEQ ID NO 25
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 25
cctggtgccg ctcgtcaccg gc 22

<210> SEQ ID NO 26
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 26
acgcgtgagc gagggcaccc cg 22

<210> SEQ ID NO 27
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 27
cgcggtgggg ctcgccaccg cg 22

<210> SEQ ID NO 28
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 28
ccgggtggtg ctggccacca ag 22

```
<210> SEQ ID NO 29
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 29

gggggtgcga tgcgggacgc gc                                              22


<210> SEQ ID NO 30
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 30

ttcggtgggg acggggacac gg                                              22


<210> SEQ ID NO 31
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 31

cagcgtgccc gccgcgacca cg                                              22


<210> SEQ ID NO 32
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 32

gttcgtgaac aaggtgaccg gt                                              22


<210> SEQ ID NO 33
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 33

gggagtgacc gacgcgacag cg                                              22


<210> SEQ ID NO 34
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 34

gctggtggcg gaggcgaggg ac                                              22


<210> SEQ ID NO 35
<211> LENGTH: 22
<212> TYPE: DNA
<213> ORGANISM: Artificial Sequence
<220> FEATURE:
<223> OTHER INFORMATION: Synthetic polynucleotide
```

<400> SEQUENCE: 35
cggcgtgccc gtggtgaccc gg 22

<210> SEQ ID NO 36
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 36
ggtggtgctc atcgagaacc gc 22

<210> SEQ ID NO 37
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 37
cgcggtggtg gccgagaacg ta 22

<210> SEQ ID NO 38
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 38
cccggtgcgg cgggtgaccc tg 22

<210> SEQ ID NO 39
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 39
ccaggtgctc ccggcgacaa cg 22

<210> SEQ ID NO 40
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 40
ggacgtggcc ggggagacgc tc 22

<210> SEQ ID NO 41
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 41
gggcgtgccc ctggtgaggt cc 22

<210> SEQ ID NO 42
<211> LENGTH: 22

-continued

```
<212> TYPE: DNA
<213> ORGANISM: Artificial Sequence
<220> FEATURE:
<223> OTHER INFORMATION: Synthetic polynucleotide

<400> SEQUENCE: 42

cctcgtggtg tgcgcgagcg ag                                              22


<210> SEQ ID NO 43
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 43

cgtggtgctc gaagtgaccg ac                                              22


<210> SEQ ID NO 44
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 44

tgaagtgggg agagtgagcc cc                                              22
```

ENGINEERED *STREPTOMYCES ALBUS* STRAINS

RELATED APPLICATIONS

This Application is a national stage filing under 35 U.S.C. § 371 of international PCT application, PCT/US2019/025948, filed Apr. 5, 2019, which claims priority under 35 U.S.C. § 119 (e) to U.S. provisional patent application, U.S. Ser. No. 62/654,145, filed Apr. 6, 2018, the entire contents of each of which is incorporated herein by reference.

FEDERALLY SPONSORED RESEARCH

This invention was made with government support under CA172319 awarded by the National Institutes of Health. The government has certain rights in the invention.

BACKGROUND

Genome sequencing revealed that *Streptomyces* sp. can dedicate up to ~10% of their genomes for the biosynthesis of bioactive secondary metabolites. However, the majority of these biosynthetic gene clusters are only weakly expressed or not at all. Indeed, the biosynthesis of natural products is highly regulated through integrating multiple nutritional and environmental signals perceived by pleiotropic and pathway-specific transcriptional regulators. Generally, pathway-specific refactoring has been the predominant approach for the activation of individual gene clusters.

SUMMARY

In some aspects, the disclosure relates to certain strains of bacterial cells (e.g., *Streptomyces* sp.) that have been genetically modified to enhance production of secondary metabolites. In some embodiments, the secondary metabolites are endogenous secondary metabolites. In some embodiments, the secondary metabolites are heterologous secondary metabolites. The disclosure is based, in part, on the discovery that modification of *Streptomyces* bacteria to lack or overexpress certain global (e.g., non-pathway-specific) metabolic regulatory genes results in a shift of bacterial metabolism to increase production of secondary metabolites.

Accordingly, in some aspects, the disclosure relates to a genetically engineered *Streptomyces* J1074 bacterium, wherein the bacterium comprises a nucleic acid having a modification to at least one global regulator gene selected from Table 1, wherein the modification is selected from a mutation, an insertion, or a deletion.

In some embodiments, a nucleic acid comprises a modification to one or more negative regulator genes. In some embodiments, one or more negative regulator gene is selected from WblA, DasR, Pfk, PhoR-PhoP, AbsA1, AbsA2, and SCO1712. In some embodiments, a modification is a deletion of WblA, a deletion of Pfk, or a deletion of WblA and Pfk. In some embodiments, a bacterium (e.g., a *Streptomyces albus* J1074 bacterium) comprises the genotype ΔwblA, Δpfk, or ΔpfkΔwblA.

In some embodiments, a nucleic acid comprises a modification to one or more positive regulator genes. In some embodiments, one or more positive regulator gene is selected from AdpA, AtrA, KbpA-AfrsKRS, AfsA-ArpA, CRP, AfsQ1, AfsQ2, RelA, RpoB, RpsL, and BldA. In some embodiments, a modification is an insertion of an additional copy of a positive regulator gene into a bacterium (e.g., a *Streptomyces albus* J1074 bacterium).

In some embodiments, a positive regulator gene is heterologous with respect to *S. albus*. In some embodiments, a positive regulator gene is a CRP gene. In some embodiments, a CRP gene is a *Streptomyces coelicolor* CRP gene (e.g., CRP$_{SC}$).

In some embodiments, a positive regulator gene is operably linked to a constitutive promoter. In some embodiments, a constitutive promoter is an ermE* promoter.

In some embodiments, a bacterium (e.g., a *Streptomyces albus* J1074 bacterium) comprises the genotype+crp$_{SC}$ or +ermE*crp$_{SC}$.

In some embodiments, a bacterium (e.g., a *Streptomyces albus* J1074 bacterium) comprises a genotype selected from: +crp$_{SC}$, +crp$_{SC}$ΔwblA, +crp$_{SC}$Δpfk, +crp$_{SC}$ΔwblAΔpfk, +ermE*crp$_{SC}$, +ermE*crp$_{SC}$ΔwblA, +ermE*crp$_{SC}$Δpfk, and +ermE*crp$_{SC}$ΔwblAΔpfk.

In some embodiments, a bacterium further comprises a deletion of one or more endogenous genes required for endogenous secondary metabolite production. In some embodiments, one or more endogenous genes comprise a gene cluster. In some embodiments, one or more endogenous genes are required for production of paulomycin (e.g., a plm gene cluster).

In some embodiments, a bacterium (e.g., a *Streptomyces albus* J1074 bacterium) comprises a genotype selected from: Aplm+crp$_{SC}$, Aplm+crp$_{SC}$ΔwblA, Aplm+crp$_{SC}$Δpfk, Aplm+crp$_{SC}$ΔwblAΔpfk, Aplm+ermE*crp$_{SC}$, Aplm+ermE*crp$_{SC}$ΔwblA, Aplm+ermE*crp$_{SC}$Δpfk, and Aplm+ermE*crp$_{SC}$ΔwblAΔpfk.

In some embodiments, a bacterium further comprises an isolated nucleic acid encoding one or more genes required for production of a secondary metabolite that is heterologous to *S. albus*. In some embodiments, the one or more genes required for production of the secondary metabolite that is heterologous to *S. albus* comprise a gene cluster.

In some embodiments, a secondary metabolite that is heterologous to *S. albus* is selected from a terpene, polyketide, non-ribosomal peptide, siderophore, lantibiotic, pyrone, steroid, and beta-lactam.

In some aspects, the disclosure relates to methods of producing a genetically engineered *Streptomyces* J1074 bacterium, comprising transforming a *Streptomyces* J1074 bacterium with an isolated nucleic acid capable of inducing an in-frame deletion of a negative global regulator gene described in Table 1.

In some embodiments of the methods, the negative global regulator gene is WblA or Pfk.

In some embodiments, the methods further comprise the step of introducing into the bacterium an isolated nucleic acid that encodes a positive global regulator gene. In some embodiments, the positive global regulator gene is CRP. In some embodiments, the CRP gene is operably linked to an ermE* promoter.

In some embodiments, a bacterium (e.g., a *Streptomyces albus* J1074 bacterium) is further modified to lack a plm gene cluster.

In some embodiments, the disclosure relates to secondary metabolites that are heterologously produced by a genetically engineered bacterium as described by the disclosure.

In some aspects, the disclosure relates to a composition comprising one or more of a genetically engineered bacterium as described by the disclosure, and a bacterial culture media.

In some aspects, the disclosure relates to a composition comprising a secondary metabolite that is heterologously produced by the genetically engineered bacterium as described by the disclosure, and an adjuvant.

BRIEF DESCRIPTION OF DRAWINGS

FIG. 1A is a schematic depicting a strategy for in-frame deletion of pfk gene in *S. albus*. FIG. 1 B shows PCR confirmation of pfk deletion; M, 1 kb ladder. Solid black arrows represent primers used for PCR screening and sizes of the PCR products are indicated. FIG. 1C shows a comparison of sensitivity to diamide (100 mM) between *S. albus* J1074 and the Δpfk-derivative strain using diamide disc assays. The table shows the diameter and area of the halo formed around a disk impregnated with diamide. Values are means of three replicates. ± standard deviation ($p<0.01$). Statistical significance was calculated with Student's t-test.

FIG. 2A is a schematic depicting a strategy for in-frame deletion of the wblA gene in *S. albus* using A-mediated recombineering. FIG. 2B shows PCR confirmation of unmarked wblA deletion in different backgrounds. M, 1 kb ladder. Solid black arrows represent primers used for PCR screening and sizes of the PCR products are indicated. FIG. 2C is a photograph indicating *S. albus* ΔwblA mutant showed a sporulation-deficient phenotype on MS agar media.

FIG. 3A shows PCR confirmation of pIJ10257-ermE*$crp_{SC}$ plasmid integration into various *S. albus* backgrounds. For the PCR screening, primers were used to amplify the coding region of $crp_{SC}$ gene. The expected size of the PCR product was 768 bp. M, 1 kb ladder. FIG. 3B shows phenotypes of *S. albus* J1074 vs *S. albus*+erm*$crp_{SC}$ cultured on MS solid media.

FIG. 4A shows LC-MS analysis of ethyl acetate extracts derived from 50 ml R5A cultures inoculated with wild-type and *S. albus* mutant strains. Cultures were grown for 6 days at 30° C. The major peaks that are present in Δwbla and [+ermE*$crp_{SC}$] backgrounds but absent in wild-type and Δpfk strains are identified as paulomycin/paulomenol molecules. Corresponding masses ($M+Na^+$) and maximum UV absorption spectra are shown. FIG. 4B shows biomass accumulation over 6-day fermentation in R5A liquid media. 25 ml media were inoculated with inoculum directly from glycerol stocks to $OD_{450}$ 0.03. Following incubation, 1 ml culture sample was removed and spun for 3 min at 14,000 rpm. Supernatants were discarded and the pellet was dried at 80° C. overnight and weighed. Values are means of three replicates. Error bars represent standard deviation. DCW dried cell weight. Deletion of $pfk_{SA}$ gene and $crp_{SC}$ overexpression has no effect on growth rate relative to wild-type whereas ΔwblA mutant accumulates ~5 times more biomass than the wild type ($p<0.0001$). Statistical significance was calculated with Student's t-test. FIG. 4C shows chemical structures of paulomenols/paulomycins compounds. Paulomenol B, calculated m/z of 661.26; paulomenol A, calculated m/z of 675.27; paulomycin B, calculated m/z of 786.25; paulomycin A, calculated m/z of 800.27. Paulic acid moiety conferring the antimicrobial activity of paulomycins is indicated with shading.

FIG. 5A is a schematic depicting a paulomycin gene cluster knockout strategy. FIG. 5B shows PCR confirmation of 15 kb deletion from the paulomycin gene cluster in different backgrounds. M, 1 kb ladder. Solid black arrows represent primers used for PCR screening and sizes of the PCR products are indicated. Confirmation of upregulation of paulomycin gene cluster (FIG. 5C) in triple mutant *S. albus* ΔpfkΔwblA+ermE*$crp_{SC}$ versus *S. albus* ΔpfkΔwblAΔplm+ermE*$crp_{SC}$ by LC-MS profiling of culture extracts produced following 6 days of growth in R5A media and (FIG. 5D) antimicrobial assay of culture extracts derived from *S. albus* and engineered strains grown for 4 days in R5A media against *Bacillus cereus*. Minimum inhibition concentration for both *S. albus*+ermE*$crp_{SC}$ and ΔwblA derived extracts are reported to be 7.8 μg/ml.

DETAILED DESCRIPTION

Figure 1A:
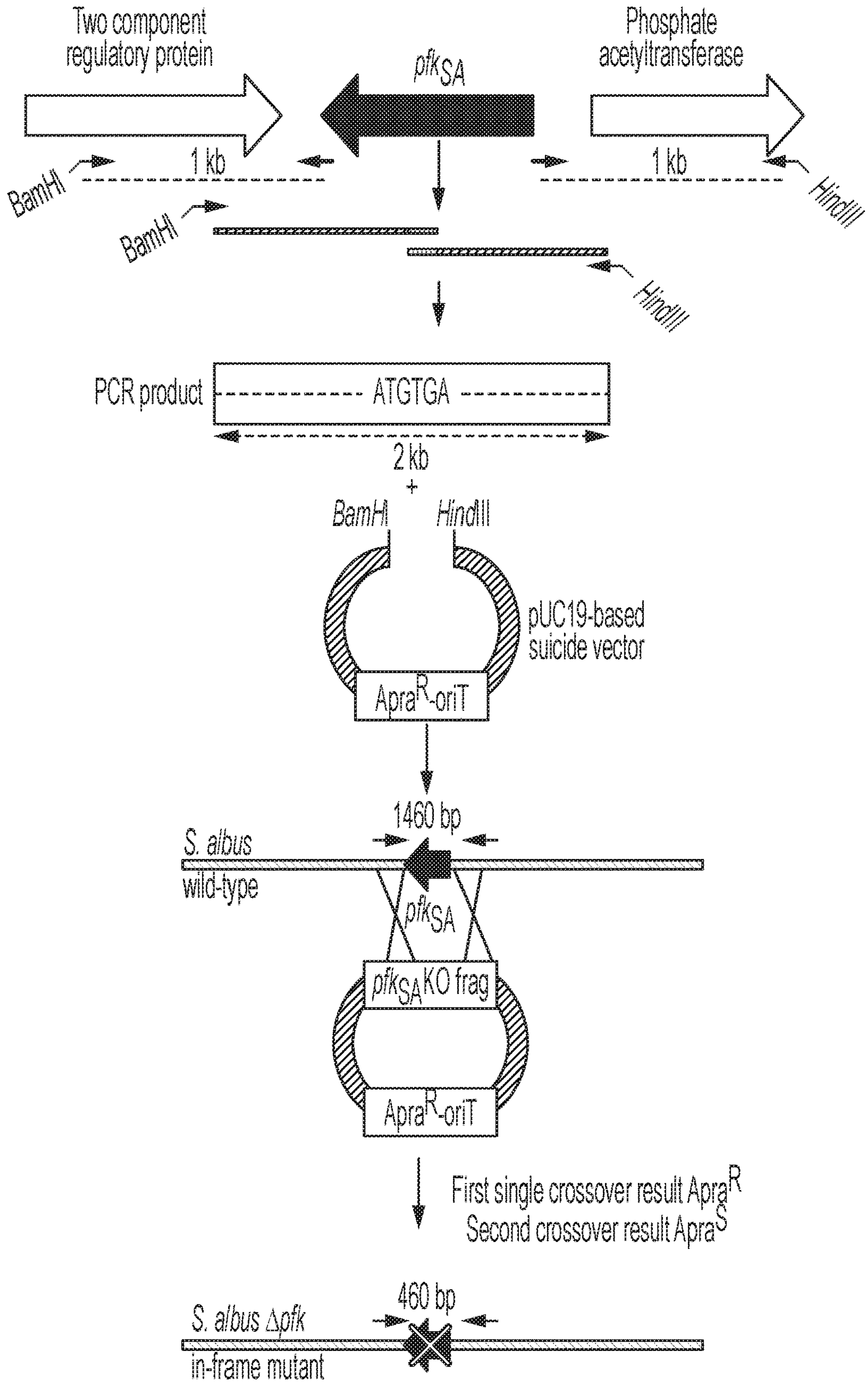
FIGS. 1A-1C show pfk genetic engineering of *S. albus* J1074 bacteria.

The disclosure relates, in some aspects, to compositions and methods useful for production of certain bacterial secondary metabolites (e.g., endogenous secondary metabolites or heterologous secondary metabolites).

As used herein, the term "secondary metabolites" refers to compounds that are not directly involved in the growth, development or reproduction of a bacterium (e.g. a *Streptomyces* bacterium, such as a *S. albus* J1074 bacterium). Secondary metabolites are not essential for the function of the primary metabolic pathways of a bacterium. They often function as defense molecules (e.g., antibiotics and toxins), transport agents or pheromones. Non-limiting examples of secondary metabolites include alkaloids, terpenoids, glycosides, natural phenols, phenazines, biphenyls, dibenzofurans and beta-lactams, polyketides (PKs), non-ribosomal peptides (NRP) and post-translationally modified peptides (RiPPs).

The disclosure is based, in part, on genetically engineered *Streptomyces albus* J1074 bacterial cells that comprise one or more modifications to global regulatory genes which control production of secondary metabolites.

Genetically Engineered Bacterial Cells

As used herein, "genetically engineered" refers to an organism having a genome that has been manipulated experimentally in any way. An organism may be genetically engineered by the addition, subtraction or mutation of a gene or genes. For example, exogenous genetic material may be introduced or delivered to an organism via transformation, transduction or injection. The addition or subtraction may be a temporary alteration, for example a transient or episomal transformation or transfection of an organism with a gene or genes. Alternatively, the addition or subtraction may be permanent, for example the integration of a gene or genes into the genome of the organism. Generally, the subtraction of a gene from a bacterium is denoted by a delta symbol followed by the gene name. For example, a bacterium that has been genetically modified to lack the phosphofructokinase (pfk) gene may be referred to as "Δpfk". Addition or insertion of a gene into a bacterium may be denoted by a "+" followed by the gene name. For example, a bacterium that has been genetically modified to include a *Streptomyces coelicolor* CRP gene ($CRP_{SC}$) may be referred to as "$+crp_{SC}$". Methods of genetic engineering are generally well known in the art and are disclosed, for example in *Molecular Cloning: A Laboratory Manual*, J. Sambrook and D. W. Russell (eds.), 3rd Ed., Cold Spring Harbor Press, New York, 2001.

In some aspects, the disclosure relates to a genetically engineered *Streptomyces* J1074 bacterium, wherein the bacterium comprises a nucleic acid having a modification to at least one global regulator gene.

*Streptomyces albus* J1074 is a strain of bacteria having the smallest genome of all completely sequenced *Streptomyces* species but maintains at least 22 putative secondary metabolic gene clusters. Without wishing to be bound by any particular theory, the minimal genome of *S. albus* J1074 and presence of secondary metabolic pathways renders this strain useful for production of secondary metabolites. The *Streptomyces albus* J1074 is generally described by Zaburannyi et al. (2014) *BMC Genomics* 15:97. The nucleotide sequence of *S. albus* J1074 genome has been deposited in the GenBank database under accession number GenBank: CP004370.

As used herein, "global regulator gene" refers to a bacterial gene (e.g., a gene present in *S. albus*) that functions in a pleiotropic (e.g., non-pathway-specific) manner to regulate bacterial metabolism. Generally, pleiotropic regulators (e.g. global regulator genes) are capable of modulating multiple biosynthetic pathways in bacteria, for example to shift the balance of bacterial metabolism from primary metabolism to secondary metabolism under conditions of cellular or environmental stress. Non-limiting examples of global regulator genes are provided in Table 1.

TABLE 1

| Global regulator | Role | Effect on Secondary Metabolism |
|---|---|---|
| WblA | Antibiotic downregulator | negative |
| AdpA | Central transcriptional regulator; AdpA represses the transcription of wblA in *S. coelicolor* | positive |
| DasR | Regulator of secondary metabolite gene expression in response to phosphorylated amino sugars | negative |
| AtrA | Transcriptional activator of actinorhodin; antagonist to DasR | positive |
| Pfk | Phosphofructokinase; key enzyme in glycolysis that controls metabolic fluxes affecting secondary metabolism | negative |
| KbpA-AfsKRS | Gene cascade linking phosphate and secondary metabolisms | positive |
| PhoR-PhoP | Two component system regulating phosphate assimilation; overlaps with AfsKRS regulon | negative |
| AfsA-ArpA | Genes required for the biosynthesis and function of γ-butyrolactone A-factor in *S. griseus* | positive |
| CRP | cAMP receptor protein; activates transcription of biosynthetic genes and controlling production of precursors; partially shared regulon with that of AfsKRS and PhoRP | positive |
| AbsA1/2 | Two component system controlling antibiotic biosynthesis in *S. coelicolor* | negative |
| AfsQ1/2 | Two component system controlling antibiotic biosynthesis in *S. lividans* | positive |
| RelA | ppGpp synthetase gene; stringent response-induced antibiotic production | positive |
| RpoB | RNA polymerase subunit; mutations conferring rifampicin resistance and mimicking stringent response-induced secondary metabolism activation | positive |
| RpsL | Encodes for S12 ribosomal protein; mutations conferring resistance to streptomycin promote secondary metabolism activation | positive |
| BldA | Encodes the tRNA for the rare leucine TTA codon found in many secondary metabolite pathway-specific regulators. | positive |
| SCO1712 | Antibiotic downregulator found in *S. coelicolor* | negative |

A global regulator gene may be a positive regulator of secondary metabolism (e.g. a "positive regulator gene") or a negative regulator of secondary metabolism (e.g., a "negative regulator gene"). Generally, positive regulator genes shift the balance of bacterial cellular metabolism to increase the production of secondary metabolites (e.g., shift away from primary metabolism), while negative regulator genes shift the balance of bacterial cellular metabolism to decrease production of secondary metabolites (e.g., shift towards primary metabolism). Examples of positive regulator genes include but are not limited to AdpA, AtrA, KbpA-AfrsKRS, AfsA-ArpA, CRP, AfsQ1, AfsQ2, RelA, RpoB, RpsL, and BldA. Examples of negative regulator genes include but are not limited to WblA, DasR, Pfk, PhoR-PhoP, AbsA1, AbsA2, and SCO1712.

The skilled artisan will appreciate that a bacterium (e.g., a *S. albus* J1074 bacterium) may be genetically engineered (e.g., modified) to lack 1, 2, 3, 4, 5, 6, 7, 8, 9, 10, or more than 10 negative regulator genes and/or genetically engineered to include (or overexpress) 1, 2, 3, 4, 5, 6, 7, 8, 9, 10, or more than 10 additional positive regulator genes. For example, in some embodiments, a bacterium (e.g., a *S. albus* J1074 bacterium) may be genetically engineered (e.g., modified) to lack any combination of negative regulator genes set forth in Table 1 and/or to include any combination of positive regulator genes set forth in Table 1.

In some embodiments, a bacterium is genetically engineered to lack a Phosphofructokinase (pfk) gene. The pfk gene functions at the branching point between glycolysis (e.g., primary metabolism) and pentose phosphate pathway (PPP) (e.g., secondary metabolism). It has been observed that deletion of this gene in *S. coelicolor* confers more resistance to the thiol oxidant diamide than the wild-type strain and results in overexpression of actinorhodin by diverting fructose-6-phosphate into PPP leading to increased levels of NADPH cofactor that is necessary for the function of many biosynthetic redox enzymes. In some embodiments, *S. albus* J1074 Δpfk strain is more resistant to diamide than the wild type *S. albus* J1074, and overexpresses the pentose phosphate pathway resulting in higher intracellular NADPH availability that allows the mutant to cope more efficiently with the oxidative stress than the wild-type. In some embodiments, increased supply of the NADPH cofactor allows genetically modified *S. albus* J1074 Δpfk to improve the production of secondary metabolites, for example herbicidal thaxtomins, whose biosynthesis relies on the NADPH-dependent function of cytochrome P450 enzymes.

In some embodiments, a bacterium is genetically engineered to lack a WblA gene. WblA, a member of the WhiB-like proteins, also has a negative effect on disulfide stress response. This family of proteins contains a [Fe—S] structural element that converts them into redox sensors. WblA has been observed to be involved in downregulation of antibiotic production.

In some embodiments, a bacterium is genetically engineered to contain one or more (e.g., 1, 2, 3, 4, 5, or more) additional copies of a positive regulator gene. In some embodiments, the positive regulator gene is cAMP receptor protein (CRP, encoded by a crp gene).

Isolated Nucleic Acids

In some embodiments, the disclosure relates to genetically engineered *Streptomyces* J1074 bacterium that comprise a nucleic acid having a modification to at least one global regulator gene. As used herein "nucleic acid" refers to a DNA or RNA molecule. An "isolated nucleic acid" refers to a nucleic acid (e.g., DNA or RNA) that has been prepared in vitro, for example by recombinant technology. Nucleic acids are polymeric macromolecules comprising a plurality of nucleotides. In some embodiments, the nucleotides are deoxyribonucleotides or ribonucleotides. In some embodiments, the nucleotides comprising the nucleic acid are selected from the group consisting of adenine, guanine, cytosine, thymine, uracil and inosine. In some embodiments, the nucleotides comprising the nucleic acid are modified nucleotides. Non-limiting examples of natural nucleic acids include genomic DNA and plasmid DNA. In some embodiments, the nucleic acids of the instant disclosure are synthetic. As used herein, the term "synthetic nucleic acid" refers to a nucleic acid molecule that is constructed via joining nucleotides by a synthetic or non-natural method. One non-limiting example of a synthetic method is solid-phase oligonucleotide synthesis. In some embodiments, the nucleic acids of the instant disclosure are isolated.

In some embodiments, an isolated nucleic acid is engineered to express a positive regulator gene. As used herein, the term "engineered to express" refers to an isolated nucleic acid that comprises a gene to be expressed (e.g., CRP, etc.) and, optionally, one or more expression control sequences. Examples of expression control sequences include but are not limited to promoter sequences, enhancer sequences, repressor sequences, poly A tail sequences, internal ribosomal entry sites, Kozak sequences, antibiotic resistance genes (e.g., ampR, kanR, a chloramphenicol resistance gene, a β-lactamase resistance gene, etc.), an origin of replication (ori), etc.

In some embodiments, one or more isolated nucleic acid is operably linked to a promoter sequence. A promoter can be a constitutive promoter or an inducible promoter. In some embodiments, a promoter is a constitutive promoter. Examples of constitutive promoters include but are not limited to constitutive *E. coli* $\sigma^{70}$ promoters, constitutive *E. coli* $\sigma^{S}$ promoters, constitutive *E. coli* $\sigma^{32}$ promoters, constitutive *E. coli* $\sigma^{34}$ promoters, constitutive *B. subtilis* $\sigma^{A}$ promoters, constitutive *B. subtilis* $\sigma^{B}$ promoters, constitutive bacteriophage T7 promoters, constitutive bacteriophage SP6 promoters, constitutive yeast promoters, etc. In some embodiments, a promoter is a constitutive *Streptomyces* promoter, for example ermE* or kasOP* as described by Wang et al. (2013) *Appl. Environ. Microbiol* 79(14):4484-4492.

In some embodiments, a promoter is an inducible promoter (e.g., induced in the presence of a small molecule, such as IPTG or tetracycline). Examples of inducible promoters include but are not limited to a promoter comprising a tetracycline responsive element (TRE), a pLac promoter, a pBad promoter, alcohol-regulated promoters (e.g., AlcA promoter), steroid-regulated promoters (e.g., LexA promoter), temperature-inducible promoters (e.g., Hsp70- or Hsp90-derived promoters, light-inducible promoters (e.g., YFI), etc.

In some embodiments, an isolated nucleic acid engineered to express a protein is a component of a vector. Examples of vectors include plasmids, viral vectors, cosmids, fosmids, and artificial chromosomes. In some aspects, one or more isolated nucleic acids engineered to express a protein (e.g., CRP, etc.) are located (e.g., situated) on a plasmid, for example a bacterial plasmid such as an F-plasmid. In some embodiments, the vector is a high-copy plasmid. In some embodiments, the vector is a low-copy plasmid. In some embodiments, a bacterial cell comprises one or more plasmids comprising the one or more isolated nucleic acids. For example, a plasmid may comprise 1, 2, 3, 4, 5, 6, 7, 8, 9, or 10 isolated nucleic acids. In some embodiments, a plasmid comprises 1, 2, or 3 isolated nucleic acids.

In some embodiments, one or more isolated nucleic acids (e.g., one or more isolated nucleic acids encoding a positive regulator gene, such as crp) are integrated into a chromosome of a bacterial cell. Methods of integrating exogenous (e.g., foreign) DNA into a bacterial chromosome are known in the art and are described, for example, by Gu et al. (2015) *Scientific Reports* 5; Article number 9684.

Secondary Metabolites

In some aspects, the disclosure relates to genetically engineered *Streptomyces* bacteria (e.g., *S. albus* J1074) that have been modified to lack one or more genes required for production of endogenous secondary metabolites. As used herein "endogenous secondary metabolite" refers to a secondary metabolite that is capable of being produced by wild-type *Streptomyces albus* J1074 bacteria (e.g., a secondary metabolite for which the gene cluster required to make the secondary metabolite is present in the genome of wild-type *S. albus*). In some embodiments, a *S. albus* J1074 bacterium is genetically engineered to lack one or more genes required for synthesis of the secondary metabolite paulomycin. In some embodiments, a *S. albus* J1074 bacterium is genetically engineered to lack a paulomycin (plm) gene cluster.

Strains of genetically engineered bacteria (e.g., *S. albus* J1074 bacteria) lacking one or more genes for endogenous secondary metabolite expression may be created by random mutagenesis and/or directed evolution. Alternatively, genetically engineered bacteria may be modified to silence expression of genes and/or gene clusters encoding endogenous secondary metabolites by CRISPER and/or RNAi. In some embodiments, genes and/or gene clusters encoding for endogenous secondary metabolites are completely removed from the genome of the genetically enhanced bacterium (e.g., a *S. albus* J1074 bacterium), for example by vector-mediated excision (VEX).

In some aspects, the disclosure relates to genetically engineered *Streptomyces* bacteria (e.g., *S. albus* J1074) that have been modified to express one or more genes required for production of heterologous secondary metabolites. As used herein "heterologous secondary metabolite" refers to a secondary metabolite that is not capable of being produced by wild-type *Streptomyces albus* J1074 bacteria (e.g., a secondary metabolite for which the gene cluster required to make the secondary metabolite is not present in the genome of wild-type *S. albus*).

As used herein, the term "gene cluster" refers to a group of two or more genes that encode for polypeptides and/or proteins that are required for the production of a secondary metabolite and are clustered together within the genome of an organism. In some embodiments, the gene cluster encodes biosynthetic proteins required for the synthesis of a bacterial secondary metabolite. Examples of biosynthetic proteins include but are not limited to enzymes, chaperone proteins, transport proteins, pre-peptides and regulatory proteins.

Accordingly, in some embodiments, genetically enhanced cyanobacteria described herein comprise a heterologous gene cluster encoding at least one biosynthetic protein necessary for production of a heterologous secondary metabolite. In some embodiments, the gene cluster encodes at least 2, at least 3, or at least 4, at least 5, at least 6, at least 7, at least 8 at least, 9 at least, at least 10, at least 11, at least 12, at least 13, at least 14, at least 15, at least 16, at least 17, at least 18, at least 19, or at least 20 biosynthetic proteins necessary for production of a heterologous secondary metabolite.

In some embodiments, a genetically engineered *Streptomyces* bacteria (e.g., *S. albus* J1074) comprises one or more genes (e.g. a gene cluster) required for production of a secondary metabolite that is useful as an antibiotic. Examples of bacterial secondary metabolites that function as antibiotics are described, for example by Awad et al. (2012) *Jurnal Teknologi* (*Sciences and Engineering*) 59:Suppl 1:101-111.

Compositions Comprising Genetically Engineered Bacterial Cells

In some aspects, the disclosure relates to a composition comprising one or more of a recombinant bacterial cell as described by the disclosure, and a bacterial culture media. As used herein, a "bacterial culture media" is a nutrient rich composition that supports growth and reproduction of bacterial cells. Generally, bacterial culture media can be liquid or solid (e.g., culture media mixed with agar to form a gel). In some embodiments, bacterial culture media is a liquid. Examples of bacterial culture media include but are not limited to M9, Lysogeny Broth (LB), SOC media, Terrific Broth (TB), etc.

The volume of bacterial culture media in a composition comprising a recombinant bacterial cell can vary depending upon several factors including but not limited to the desired amount of nitrated aromatic compounds to be produced, the concentration (density) of bacterial cells desired in the composition, the volume of the container housing the composition, etc. In some embodiments, a composition comprises between about 10 μl and 1 L bacterial culture media. In some embodiments, a composition comprises between about 10 μl and about 1 mL bacterial culture media, for example about 10 μl, about 50 μl, about 100 μl, about 500 μl, about 750 μl, or about 1 mL (e.g., any volume between 10 μl and 1 mL, inclusive). In some embodiments, a composition comprises between about 750 μl and 5 mL (e.g., any volume between 750 μl and 5 mL, inclusive). In some embodiments, a composition comprises between about 2 mL and about 20 mL bacterial culture media (e.g., any volume between 2 mL and 20 mL, inclusive). In some embodiments, a composition comprises between about 10 mL and about 200 mL bacterial culture media (e.g., any volume between 10 mL and 200 mL, inclusive). In some embodiments, a composition comprises between about 100 mL and about 500 mL bacterial culture media (e.g., any volume between 100 mL and 500 mL, inclusive). In some embodiments, a composition comprises between about 250 mL and about 1 L bacterial culture media (e.g., any volume between 250 mL and 1 L, inclusive). In some embodiments, a composition comprises more than 1 L (e.g., 5 L, 10 L, 100 L, 200 L, 1000 L, 10,000 L, 50,000 L, etc.) bacterial culture media.

In some embodiments, a composition further comprises one or more antibiotic agents. In some embodiments, one or more antibiotic agent is ampicillin or kanamycin. A composition may comprise 1, 2, 3, 4, 5, 6, 7, 8, 9, 10, or more antibiotic agents. The concentration of an antibiotic agent can vary. In some embodiments, the concentration of an antibiotic agent ranges from about 0 (e.g., lacking antibiotic) to about 125 μg/ml.

The skilled artisan recognizes that the conditions under which a composition as described herein is maintained may affect the production and/or stability of nitrated aromatic compounds by the recombinant bacterial cell(s). The disclosure is based, in part, on the recognition that production of nitrated aromatic compounds is reduced or absent at temperatures at which bacterial cells are generally cultured (e.g., 37° C.). In some embodiments, a composition has a temperature below 37° C. (e.g., the temperature of the bacterial culture media of a composition is below 37° C.). The disclosure is based, in part, on the recognition that production of nitrated aromatic compounds is increased at temperatures between 10 to 30° C. (e.g., 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., or 30° C.). In some embodiments, a composition has a temperature of 28° C. (e.g., the temperature of the bacterial culture media of a composition is 28° C.).

In some embodiments, a composition as described by the disclosure comprises additional components, for example one or more cryopreservatives (e.g., glycol, DMSO, PEG, glycerol, etc.), antifungals, etc.

In some embodiments, a composition as described by the disclosure comprises additional adjuvants, for example, sugars, such as lactose, glucose and sucrose; starches such as corn starch and potato starch; cellulose and its derivatives such as sodium carboxymethycellulose, ethylcellulose and cellulose acetates; powdered tragancanth; malt; gelatin; talc; stearic acids; magnesium stearate; calcium sulfate; vegetable oils, such as peanut oils, cotton seed oil, sesame oil, olive oil, corn oil and oil of *theobroma*; polyols such as propylene glycol, glycerine, sorbitol, manitol, and polyethylene glycol; agar; alginic acids; pyrogen-free water; isotonic saline; and phosphate buffer solution; as well as other non-toxic compatible substances used in pharmaceutical formulations. Wetting agents and lubricants such as sodium lauryl sulfate, as well as coloring agents, flavoring agents, lubricants, excipients, tableting agents, stabilizers, anti-oxidants and preservatives, can also be present.

Methods of Producing Genetically Engineered Bacterial Cells

In some embodiments, the disclosure relates to methods of producing a genetically engineered bacterial cell as described by the disclosure. Typically, the methods comprise the steps of: transforming a bacterial cell with an isolated nucleic acid engineered to 1) cause a deletion (e.g., an in-frame deletion) of a negative regulator gene from the bacterium, and/or 2) insert one or more copies of a positive regulator gene into the bacterium; and culturing (e.g., growing) the bacterial cell.

Methods of introducing vectors into bacteria are well known in the art and described, for example, in Current Protocols in Molecular Biology, Ausubel et al. (Eds), John Wiley and Sons, New York, 2007. Methods of gene deletion from a bacterial genome are also known, and are described for example by Du et al. (2015) *Sci. Rep.* 5:8740.

EXAMPLES

Example 1: Materials and Methods

Bacterial Strains and Media Used

Bacterial strains used were *S. albus* J1074 and derivative mutants constructed in this example. *Escherichia coli* EPI300 (Epicentre) and S17.1 strains were used for sub-cloning and intergeneric conjugation, respectively. Growth medium for *S. albus* was tryptone soy broth (TSB) for genomic DNA isolation, and mannitol-soy flour agar (MS) was used for sporulation and R5A as regular production medium. LB medium was used for routine *E. coli* growth. When plasmid-containing clones were grown, media were supplemented with appropriate antibiotics: ampicillin (100 μg/mL), hygromycin (100 μg/ml), apramycin (50 μg/mL), chloramphenicol (12.5 μg/mL), when required.

*S. albus* J1074 Genomic DNA Isolation and Fosmid DNA Library Construction

Genomic DNA was isolated from *S. albus* mycelia collected from 2-day cultures grown in TSB. The mycelia pellet was lysed with lysozyme solution (0.5M sucrose, 25 mM Tris-HCl, 5 mM EDTA and 2 mg/ml lysozyme) at 37° C. for 30 min. EDTA and SDS were added to 50 mM and 0.5% (final concentration) respectively. After thorough mixing, ⅓ volume of phenol/chloroform was added and mixed to emulsify. The mixture was spun at 10,000 rpm for 10 min at 4° C. and DNA was precipitated from the aqueous phase with 0.7 vol isopropanol in the presence of 1/10 vol sodium acetate, pH 5.5. The DNA pellet was washed with 70% ethanol, air-dried and resuspended in TE buffer. Fosmid DNA library was constructed using the CopyControl HTP fosmid production kit (Epicentre) following the manufacturer's instructions.

In-Frame Phosphofructokinase $pfk_{SA}$ Gene (XNR_1407) Deletion

A suicide vector for *Streptomyces* gene deletions through homologous recombination was constructed based on pUC19 (New England Biolabs) (FIG. 1A). The vector was digested with ScaI and EcoRI and ligated with DraI-EcoRI fragment from pOJ436 carrying the oriT-apramycin cassette. Primers ALpfk1 5'-ATCGGGATCCTGGTCGACAACGC-GATGGAGG-3 (SEQ ID NO: 1) and ALpfk2 5'-AGCAG-GAGAGACAGCACGATGTGAACCGGCTCCGCG CACACG-3' (SEQ ID NO: 2) were used to amplify 1 kb flanking region downstream of pfk gene. Primers ALpfk3 5'-CGTGTGCGCGGAGCCGGTTCA-CATCGTGCTGTCTCTCCTGCT-3' (SEQ ID NO: 3) and ALpfk4 5'-ATCGAAGCTTGCCCAGCAGAACC GTTCCGTC-3' (SEQ ID NO: 4) were used to amplify 1 kb flanking region upstream of pfk gene. Engineered restriction sites are underlined in the primer sequences and the start/stop codon fusion site is in italics. Standard 20 μl PCR reaction mix contained 1×G buffer (Epicentre), 50 μmol of each primer, 2.5UTaq polymerase (New England BioLabs), and 100 ng gDNA. A 2-step PCR protocol was used with the following conditions: 1 cycle at 95° C. followed by 30 cycles consisting of 40 s at 95° C. and 3 min at 72° C., followed by a final extension at 72° C. for 5 min. The two PCR products were gel-purified and used as a template for overlapping PCR (same protocol as before) with primers ALpfk1 and 4 to generate a 2 kb fragment. The PCR product was gel-purified and digested with BamHI and HindIII and ligated to the described suicide vector that has been similarly digested. *E. coli* S17.1 strain was transformed with the resulting plasmid and used for conjugal transfer into *S. albus*. Apramycin resistant colonies carrying single crossover were streaked on MS agar plates with no selection for sporulation. Spores were diluted to yield single colonies and spread on MS agar plates. Double crossover mutants were identified by replica plating using Difco nutrient agar (DNA) plates with/out apramycin selection (10 μg/ml). Correct deletion of the target gene in the mutant chromosome was further verified via PCR amplification using primers ALpfkconfF 5'-GAGGTCGGCATCTCCCGCATC-3' (SEQ ID NO: 5) and ALpfkconfR 5'-ACTCCGACGA-TACCGGTGCG-3' (SEQ ID NO: 6). PCR reaction mix was the same as before and PCR protocol was 1 cycle at 95° C. followed by 30 cycles consisting of 40 s at 95° C., 40 s at 58° C. and 40 s at 72° C., followed by a final extension at 72° C. for 5 min.

In-Frame $wblA_{SA}$ Gene (XNR_2735) Deletion

Figure 2A:
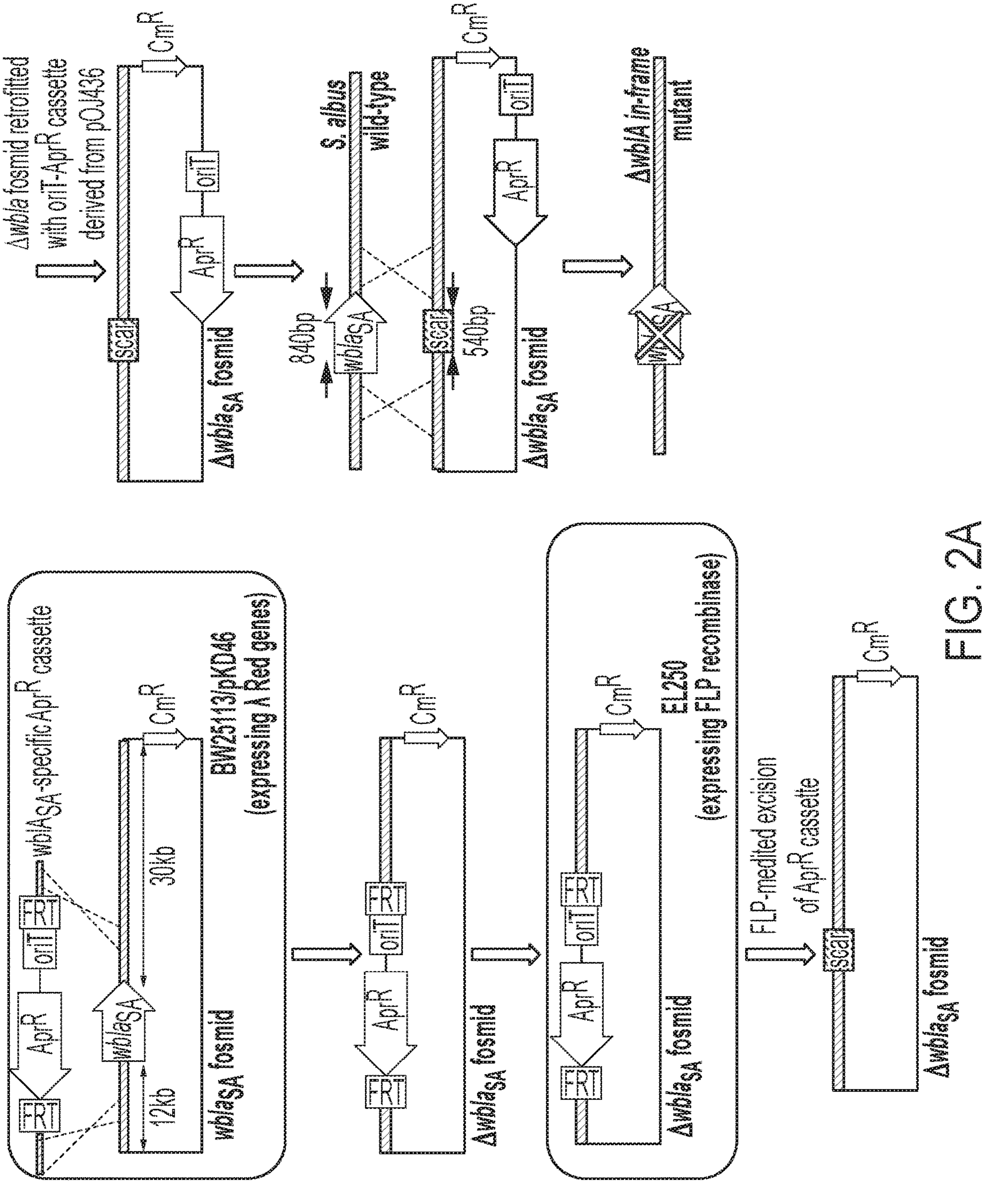
FIGS. 2A-2C show wblA genetic engineering of *S. albus* J1074 bacteria.

The *S. albus* fosmid library was screened by PCR using primers ALwblAF 5'-CCATCGGCACGTACCTGGCC-3' (SEQ ID NO: 7) and ALwblAR 5'-ATGTCCTTCCTGTCCCCGGC-3' (SEQ ID NO: 8). A single fosmid containing the full-length $wblA_{SA}$ gene was recovered by PCR screening of serially diluted, PCR-positive library pools. PCR reaction mix contained 1×G buffer (Epicentre), 50 μmol of each primer, 2.5UTaq polymerase (New England BioLabs) and 1 μl of the corresponding library pool and the PCR protocol was 1 cycle at 95° C. followed by 30 cycles consisting of 40 s at 95° C., 40 s at 57° C. and 40 s at 72° C., followed by a final extension at 72° C. for 5 min. The wblA ortholog was deleted using A-mediated recombineering approach (FIG. 2A). The $wblA_{SA}$-specific aac(3)IV-oriT resistance cassette flanking by two FRT sites was amplified from pIJ773 using primers SΔwblAredF 5'-TGGGGGAGCCTCGATTCGG-GAGAGGACGGCGCCGGTATGATTCCGGGGATCCGT CGACC-3' (SEQ ID NO: 9) and SawblAredR 5'-GGTTCCCGTACTCCTCGCTCGCCCTTGCCGGCCG GTCTATGTAGGCTGGAGCTGC TTC-3' (SEQ ID NO: 10). The amplified cassette was transformed into *E. coli* BW25113/pKD46 containing the recovered $wblA_{SA}$-containing fosmid and transformants were selected on apramycin and chloramphenicol LB agar plates. Gene replacement was confirmed by PCR analysis of the mutated ($\Delta wblA_{SA}$) fosmid using ALwblAF/R primers. To generate seamless gene deletion, the mutated fosmid was transformed into *E. coli* EL250 strain expressing FLP recombinase that catalyzes the recombination between the FRT sites. Following induction with L-arabinose, the excision of the apramycin resistant cassette was detected by patching single colonies on LB agar plates with/out 50 μg/ml apramycin. In-frame deletion mutants were verified by PCR using ALwblAF/R primers as before. The confirmed mutated fosmid was retrofitted with oriT-apramycin cassette by λ-mediated recombineering using primers

```
pCCFRedF
                                    (SEQ ID NO: 11)
5'-GTAACCTCGGTGTGCGGTTGTATGCCTGCTGTGGATTGCCGCAACGT
TGTTGCCATTGC-3'
and

pCCFRedR
                                    (SEQ ID NO: 12)
5'-AGCGATGAGCTCGGACTTCCATTGTTCATTCCACGGACAAATCCCCG
ATCCGCTCCACG-3'.
```

The cassette was amplified from pOJ436. The pCCF2 cloning vector sites targeted for recombination are underlined in the primer sequences. The final retrofitted and mutated wblA$_{SA}$-containing fosmid was introduced into *E. coli* S17.1 cells for conjugation into *S. albus*. Double crossover mutants were confirmed by PCR using ALwblAF/R primers.

Overexpression of Crp$_{SC}$ Gene from *S. coelicolor* M145 (SCO3571) in *S. albus* J1074

A crp overexpression plasmid was made by cloning the crp$_{SC}$ gene and its downstream sequence immediately downstream of the ermE* promoter in the pIJ10257 vector. The crp coding sequence was PCR amplified from *S. coelicolor* M145 gDNA using primers CrpF 5'-GAGAACTCATATGGACGACGTTC-3' (SEQ ID NO: 13) and CrpR 5'-CGTAAGCTTGGCCTAGGTCGCAGGGAC-3' (SEQ ID NO: 14). Engineered NdeI and HindIII sites in the forward and reverse primer, respectively, is underlined. PCR cycling conditions were 1 cycle at 95° C. followed by 30 cycles consisting of 40 s at 95° C., 40 s at 58° C. and 40 s at 72° C., followed by a final extension at 72° C. for 5 min. PCR product was gel-purified, digested with NdeI/HindIII and ligated to similarly digested pIJ10257 plasmid. Recombinant plasmid was introduced into *E. coli* S17.1 cells for conjugation into *S. albus*. Exconjugants were selected on MS agar plates supplemented with 25 μg/ml nalidixic acid and 50 μg/ml hygromycin.

Knock-Out of Paulomycin Gene Cluster

Figure 5A:
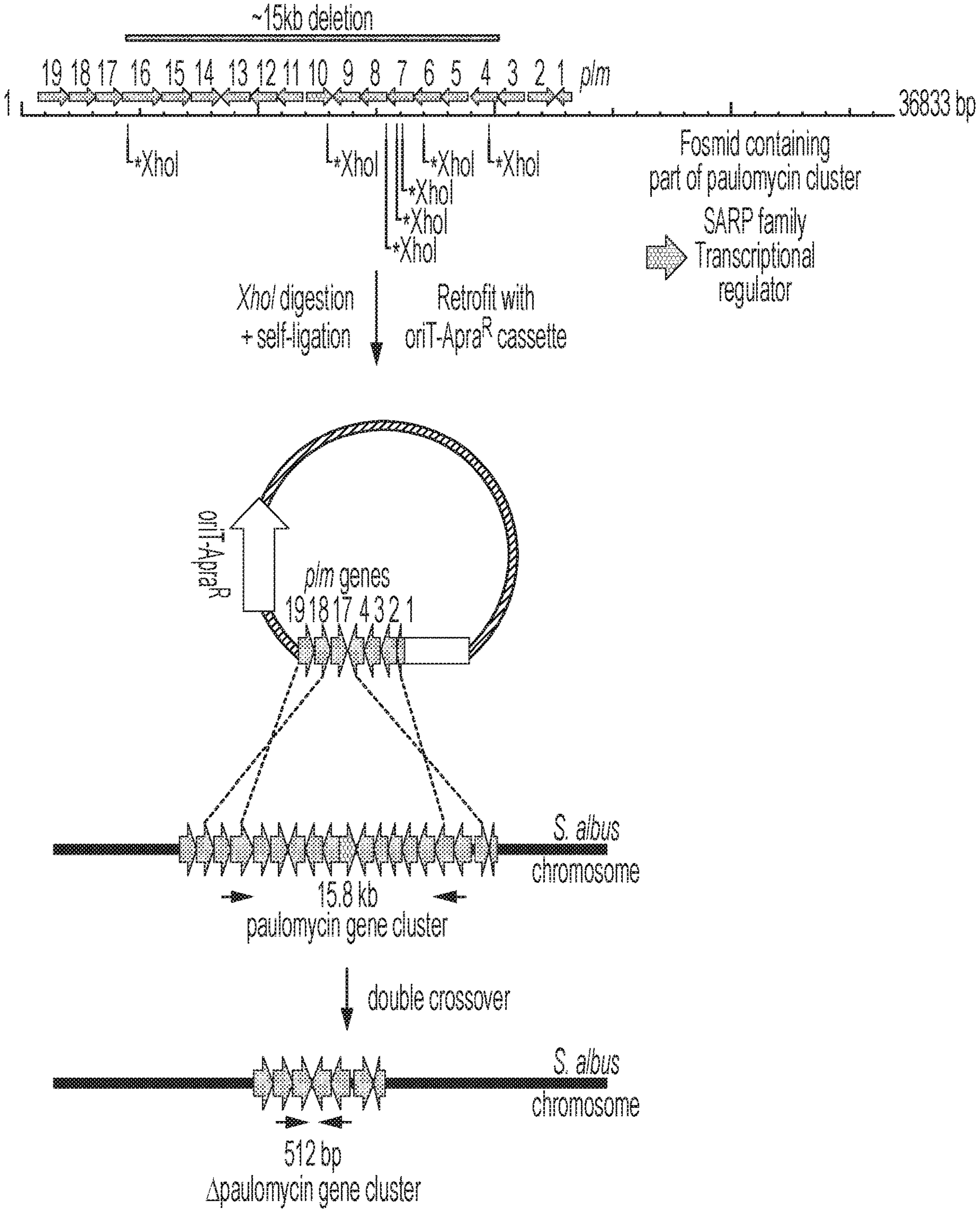
FIGS. 5A-5D shows genetic engineering of the paulomycin gene cluster in *S. albus* J1074 bacteria.

For the isolation of paulomycin gene cluster, the *S. albus* fosmid library was screened by PCR using primers pml10F 5'-GGGATTCCCTGAGCGGAGTAC-3' (SEQ ID NO: 15) and pml10R 5'-GGTTTCCAGGGGCCCTTCTAG-3' (SEQ ID NO: 16). A single fosmid containing pml1-pml19 genes (entire gene cluster contains 42 genes) was recovered by PCR screening of serially diluted, PCR-positive library pools. PCR conditions were the same as used for wblA$_{SA}$-containing fosmid isolation. The recovered plm fosmid was digested with XhoI restriction enzyme and subsequently self-ligated to eliminate 13 genes out of 19 cloned pml genes including pml10 pathway-specific regulator required for the transcriptional activation of the gene cluster (FIG. 5A). The resulting minimized plm fosmid was retrofitted with oriT-apramycin cassette by recombineering as before and introduced into *E. coli* S17.1 cells for conjugation into *S. albus* and derivative mutants. Double crossover mutants were confirmed by PCR using ΔpaulconfF 5'-GAAACCGCTCCGTCCGTCCGACACC-3' (SEQ ID NO: 17) and ΔpaulconfR 5'-TGCATCCGCAGCACCAGCAGG-3' (SEQ ID NO: 18) primers. PCR conditions were 1 cycle at 95° C. followed by 30 cycles consisting of 40 s at 95° C., 40 s at 60° C. and 40 s at 72° C., followed by a final extension at 72° C. for 5 min.

Cloning and Site-Specific Integration of Actinorhodin Gene Cluster into *S. albus* J1074 and Derivative Strains For the isolation of actinorhodin gene cluster, the *S. coelicolor* fosmid library was screened by PCR using primers Act85F 5'-CTTAAATCCTCGAAGGCGAC-3' (SEQ ID NO: 19) and Act85R 5'-GCGCCCATCAGTTTGGCGTG-3' (SEQ ID NO: 20). PCR conditions were 1 cycle at 95° C. followed by 30 cycles consisting of 40 s at 95° C., 40 s at 55° C. and 40 s at 72° C., followed by a final extension at 72° C. for 5 min. Four PCR-positive single clones were recovered. Two clones contained partial actinorhodin gene cluster and the other two harbored actinorhodin gene cluster with different sizes of flanking regions. The fosmid with the largest DNA sequence flanking the entire actinorhodin gene cluster (SCO5067-SCO5104) was subsequently retrofitted with oriT-Apra$^R$ cassette. For that, pOJ436 plasmid was double digested with PmlI-SmaI and 1.8 kb fragment containing the cassette was gel-purified and ligated with PsiI-digested and dephosphorylated actinorhodin-containing fosmid. Correct recombinant fosmid was confirmed by PCR using primers Act85F/R as above and used to transform *E. coli* S17.1 cells for conjugation into *S. albus* strains. Blue-pigmented exconjugants were selected on MS agar plates supplemented with 25 μg/ml nalidixic acid and 50 μg/ml apramycin and verified for the actinorhodin integration by PCR.

Actinorhodin Production and Antimicrobial Assays

Three biological replicates were tested using three confirmed colonies from each conjugation of actinorhodin cluster into *S. albus* J1074, *S. albus*+pIJ10257ermE*crp and *S. albus* Δpfk+pIJ10257ermE*crp. These colonies were streaked on MS agar plates to yield fully confluent spore lawns. Following 6 days of incubation at 30° C., the agar from each plate was cut into small pieces and immersed into 50 ml of 1M KOH. The tubes were left overnight at 4° C. with agitation. The samples were then spun at 4,000×g for 10 min and the absorbance of the supernatant was measured at 640 nm. Actinorhodin concentration was calculated according to the Lambert-Beer's law using molar extinction coefficient of 25,320 $M^{-1}$ $cm^{-1}$ that corresponds to pure actinorhodin.

*Bacillus cereus* overnight cultures grown in LB were diluted by $10^6$-fold. Aliquots (100 μl) of the diluted culture were added to individual wells of a 96-well plate starting from the second column. Diluted culture (195 μl) were then added to the wells of the first column. Crude organic extracts were resuspended in methanol at 20 mg/ml. These solutions (5 μl) were added to the wells of the first column in the microtiter plate and then serially diluted twofold per well across the plate. The plates were incubated at 30° C. for 18-24 h. Concentration of 500, 250, 125, 62.5, 31.25, 15.6, 7.8, 3.9, 1.95, 0.97, 0.48, 0.24 μg/ml were tested for each crude extract. The final methanol concentration was kept at 2.5%. Minimum inhibitor concentrations are reported as the lowest concentration at which no bacterial growth was observed.

Diamide Sensitivity Assays

Lawns of *S. albus* J1074 wild-type and Δpfk mutant were generated by overlaying R5A plates (sucrose 100 g/l, $K_2SO_4$ 0.25 g/l, $MgCl_2$ 10.12 g/l, glucose 10 g/l, Casamino acids 0.1 g/l, yeast extract 5 g/l, MOPS 21 g/l, NAOH 2 g/l, R2YE trace elements 2 ml/1, 15 g/L agar) with 3 ml soft Nutrient Agar containing $10^7$ fresh spores. Immediately after plating, paper discs soaked in 100 mM diamide were added and plates were incubated at 30° C. for 24 h.

Crude Extract Production for Screening

Crude extracts for screening purposes were generated from 50-mL cultures of *S. albus* strains and derivative mutants grown in R5A liquid media. After 6 days of growth, cultures were extracted twice with an equal volume of ethyl acetate and the dried extracts were then used for screening.

LC-MS Profiling of Engineered *S. albus* Secondary Metabolite Content

Crude extracts were dissolved in LC-MS grade methanol and centrifuged for 30 min. The resulting clear supernatant (10 μl) was used for LC-MS analysis. A SHIMADZU Prominence UPLC system fitted with an Agilent Poroshell 120 EC-C18 column (2.7 μm, 4.6×50 mm) coupled with a Linear Ion Trap Quadrupole LC/MS/MS Mass Spectrometer system was used in the studies. Acetonitrile (B)/water (A) containing 0.1% formic acid were used as mobile phases with a linear gradient program (10-99% solvent B over 40 min) to separate chemicals by the above reverse phase HPLC column. The column at 30° C. was eluted first with 10% solvent B (acetonitrile with 0.1% formic acid) for 3 min and then with a linear gradient of 10-50% solvent B in 15 min, followed by another linear gradient of 50-99% solvent B in 12 min. After eluting in 99% solvent B for 5 min, the linear gradient of 99-10% solvent B in 1 min was used. The column was further re-equilibrated with 10% solvent B for 4 min. The flow rate was set as 0.5 mL/min, and the products were detected by a PDA detector. For MS detection, the turbo spray conditions included curtain gas: 30 psi; ion spray voltage: 5500 V; temperature: 600° C.; ion source gas 1:50 psi; ion source gas 2:60 psi). For MS/MS analysis, the collision energy was 12 eV.

Example 2: Genetic Engineering of *S. albus* J1074 Bacteria

SCO5426 was investigated as the first gene probe encoding one of the three phosphofructokinases found in the *S. coelicolor* genome that has been observed to upregulate actinorhodin through increased carbon flux into the pentose phosphate pathway. Blast analysis identified the orthologue gene in *S. albus* genome that shares 89% nucleotide homology, designated as $pfk_{SA}$. The left-side flanking regions of $pfk_{SA}$ are conserved in both strains as the gene is located next to a cluster of three genes (phosphate acetyltransferase, acetate kinase and pyruvate kinase) involved in pyruvate metabolism. Similarly, the gene $wblA_{SA}$ was investigated and that gene showed 87% identity to $wblA_{SC}$ and $SCO1712_{SA}$ with 76% sequence homology to $SCO1712_{SC}$. An in-frame deletion of $pfk_{SA}$ was constructed using a pUC19-based suicide vector where the ampicillin resistance gene was replaced with oriT-apramycin cassette for transfer and selection in *Streptomyces*. The vector harbors two fragments of ~1 kb upstream and downstream flanking regions of pfk gene that have been fused together at start and stop codons of the gene by overlapping PCR.

Figures 1B, 1C:
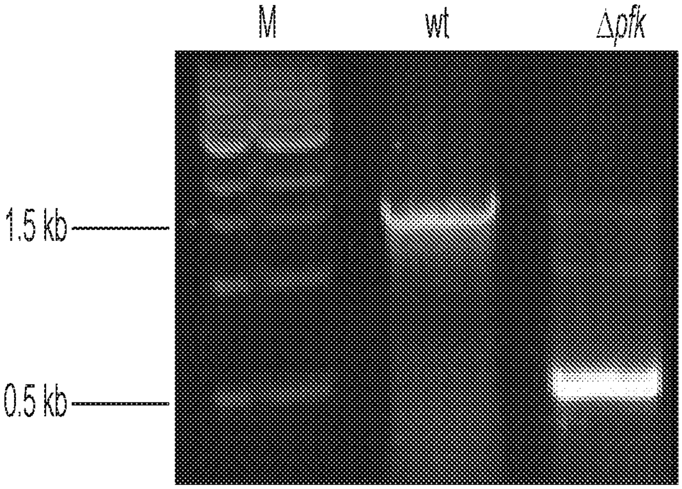

The plasmid was conjugated into *S. albus* and double crossover mutants were verified by PCR of $Apra^S$ colonies (FIGS. 1A-1B). Wild type and $\Delta pfk_{SA}$ showed no difference when they grew on MS plates but $\Delta pfk_{SA}$ mutant was less sensitive to diamide (FIG. 1C). Diamide is an artificial thiol oxidant that forms protein intramolecular disulfide bonds. The reduction of these toxic disulfide bonds is achieved through the action of thioredoxin/thioredoxin reductase system in the presence of NADPH. Similar to pfk deletion in *S. coelicolor*, carbon flux towards pentose phosphate pathway due to pfk deletion, in some embodiments, results in a higher level of NADPH that makes *S. albus* Δpfk mutant more resistant to diamide oxidant.

Figure 2B:
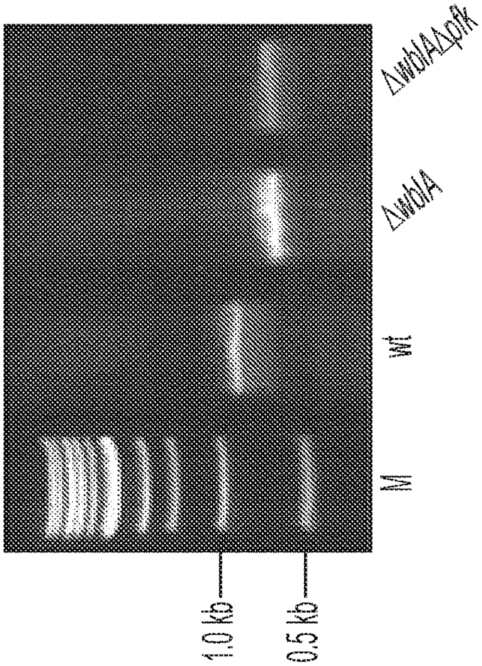
Figure 2C:
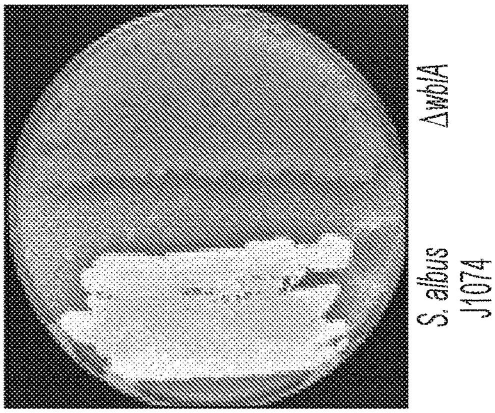

For generating $wblA_{SA}$ deletion mutant, a fosmid library of *S. albus* J1074 was constructed and screened for wblA sequences. A single fosmid containing the full-length gene was recovered and ReDirect protocol was used to replace $wblA_{SA}$ gene with apramycin marker flanked by FRT sites, which was subsequently removed by FLP recombinase resulting in fosmid with seamless $wblA_{SA}$ deletion (FIGS. 2A-2B). The resulting mutagenized fosmid was conjugated into *S. albus* and exconjugants were PCR-screened for double crossover mutant identification (FIGS. 2A-2B). The $\Delta wblA_{SA}$ mutants failed to sporulate (FIG. 2C). $\Delta wblA_{SA}$ mutants also accumulated more biomass (~5-fold) relative to wild type when they grew in R5A media (FIG. 4B). Multiple attempts to knock out $SCO1712_{SA}$ using either Red/ET recombineering or CRISPR-Cas9 systems were proved fruitless, indicating that $SCO1712_{SA}$ may have an essential role in *S. albus* growth cycle.

Figure 3A:
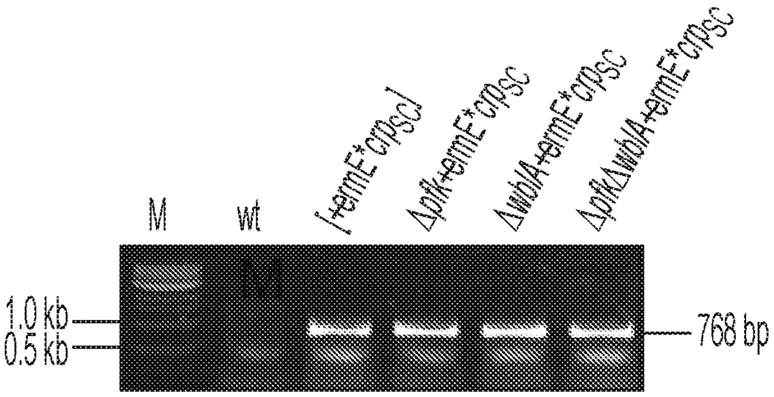
FIGS. 3A-3B show genetic crp engineering of *S. albus* J1074 bacteria.
Figure 3B:
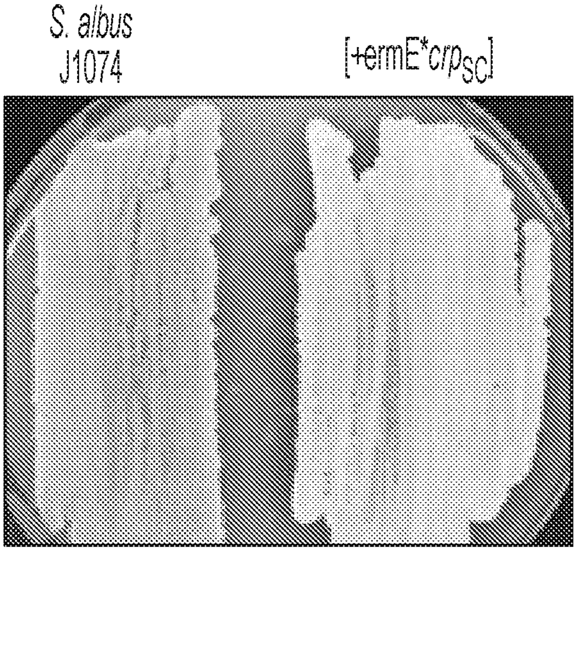

In order to combine the positive role of crp global regulator on secondary metabolism to the above mutants, the crp gene from *S. coelicolor* was heterologously inserted into *S. albus* chromosome under the control of a strong constitutive promoter. The coding region of $crp_{SC}$ was PCR-amplified, cloned into pIJ10257 conjugative integrative plasmid downstream of ermE*p and transferred in *S. albus* derivative strains using hygromycin selection (FIG. 3A). The overexpression of $crp_{SC}$ gene had no effect on the growth rate of *S. albus* in R5A liquid media (FIG. 4B) but interfered with the sporulation process resulting in a white phenotype relative to wild type when *S. albus* grew on MS solid media (FIG. 3B).

Profiling of the Secondary Metabolite Content in Engineered *S. albus* Strains

Figure 4A:
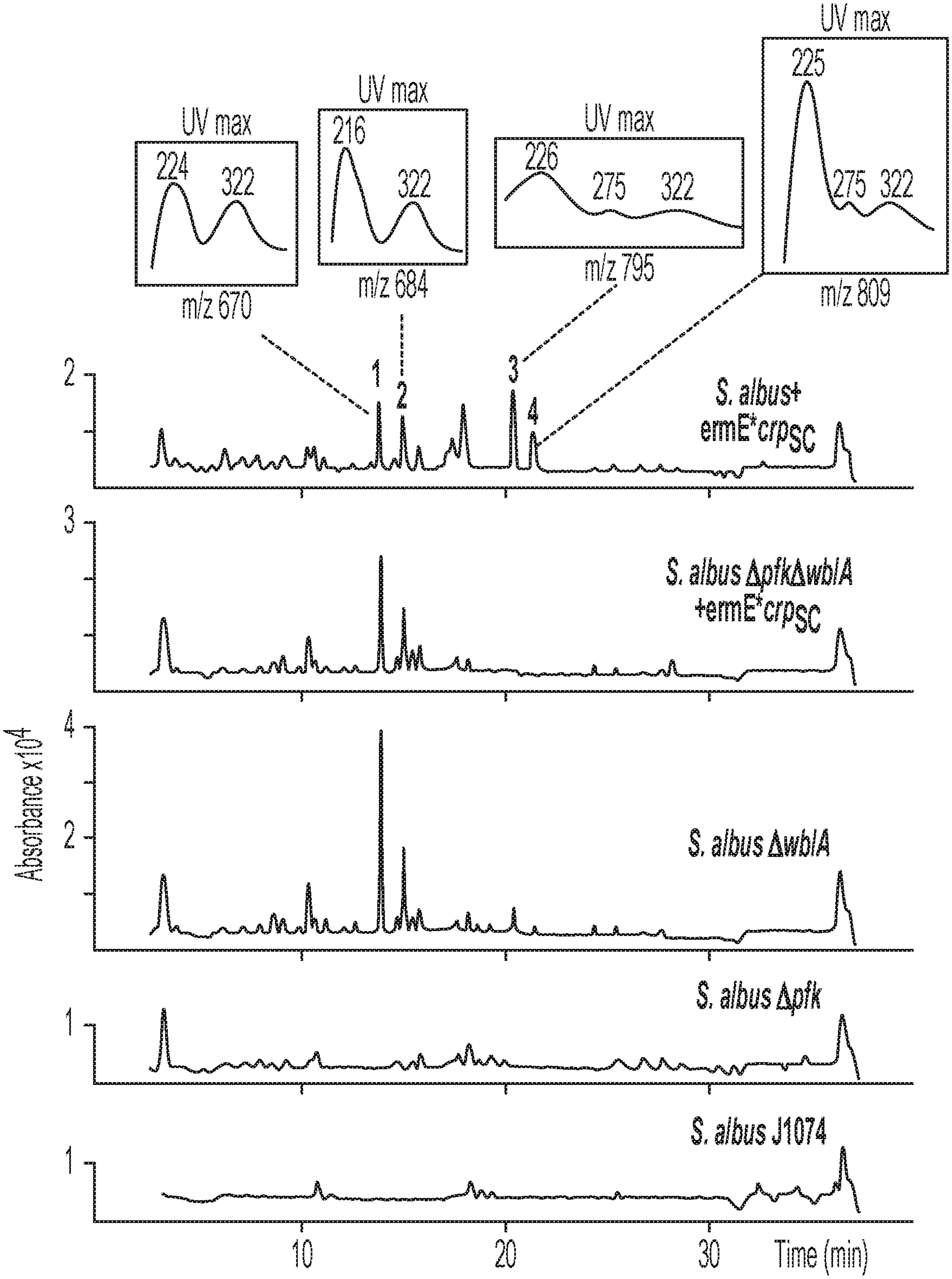
FIGS. 4A-4C show $crp_{SC}$ genetic engineering of *S. albus* J1074 bacteria.
Figure 4B:
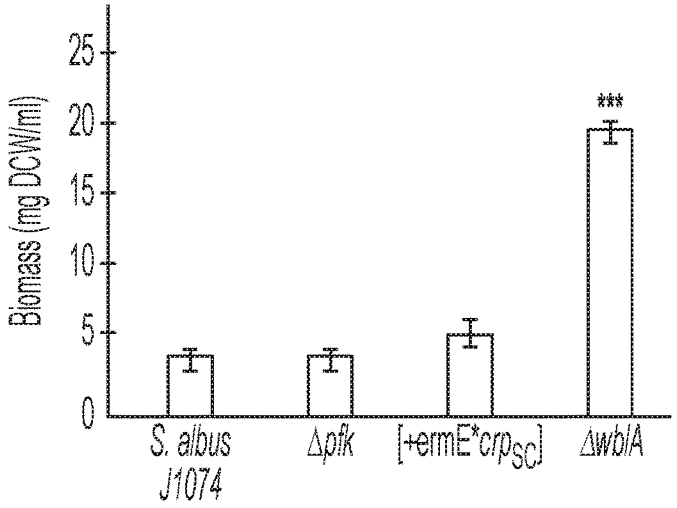
Figure 4C:
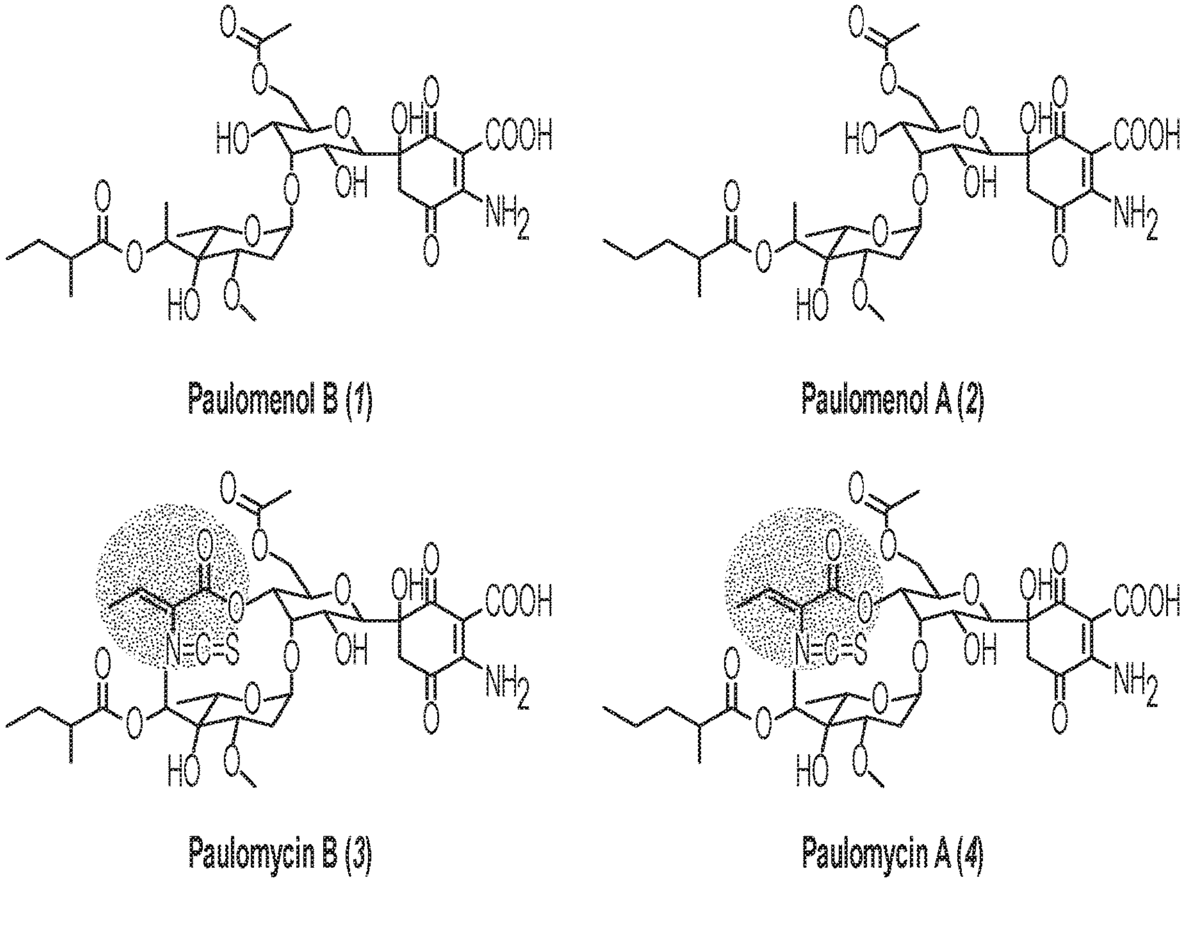
Figure 5B:
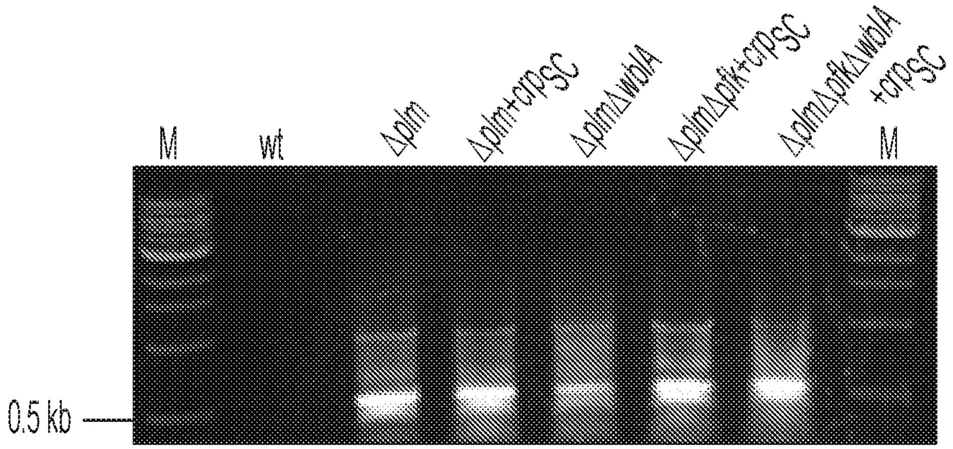
Figure 5C:
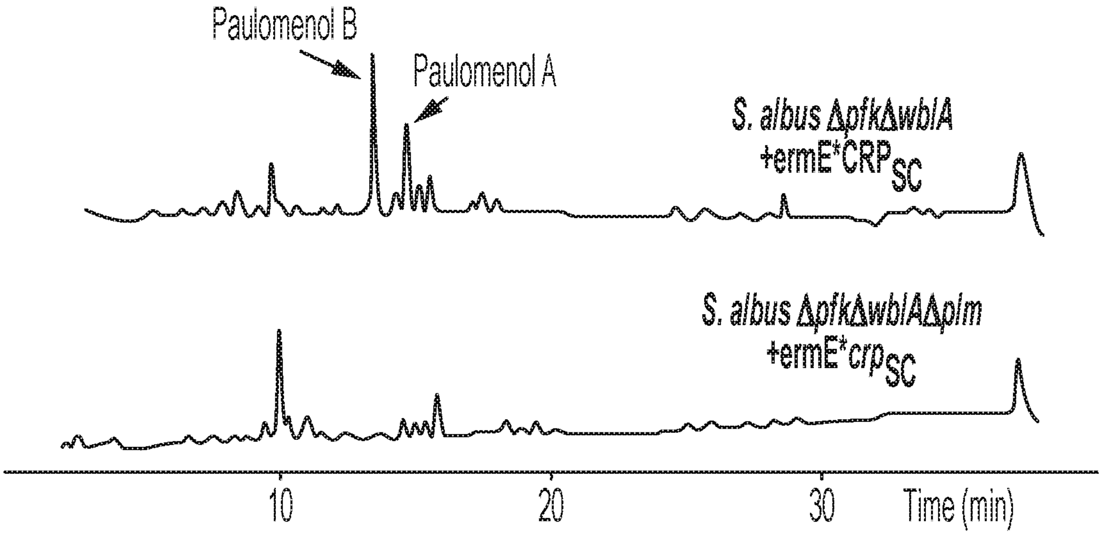
Figure 5D:
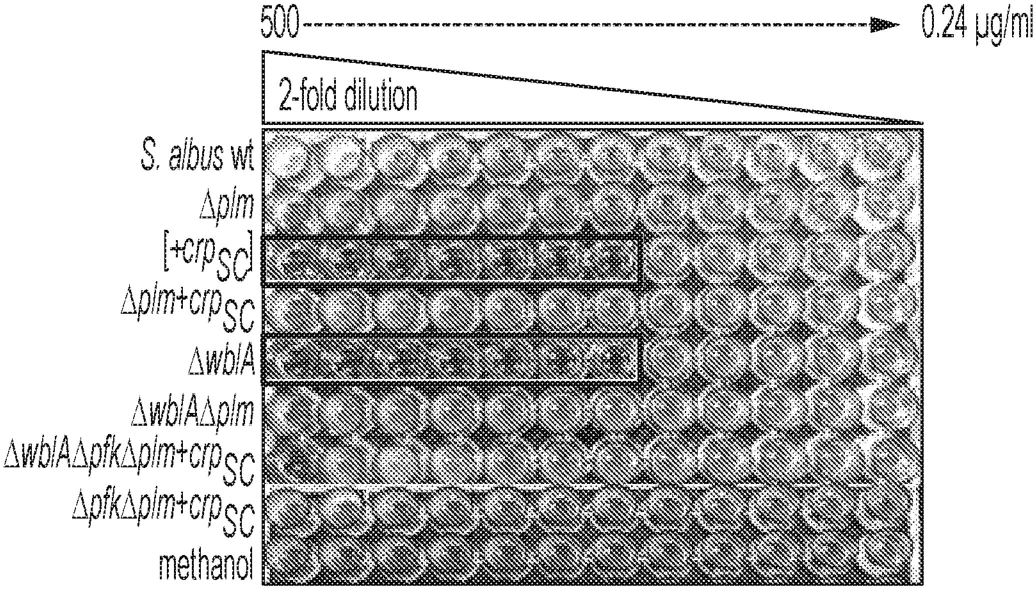
Figure 9:
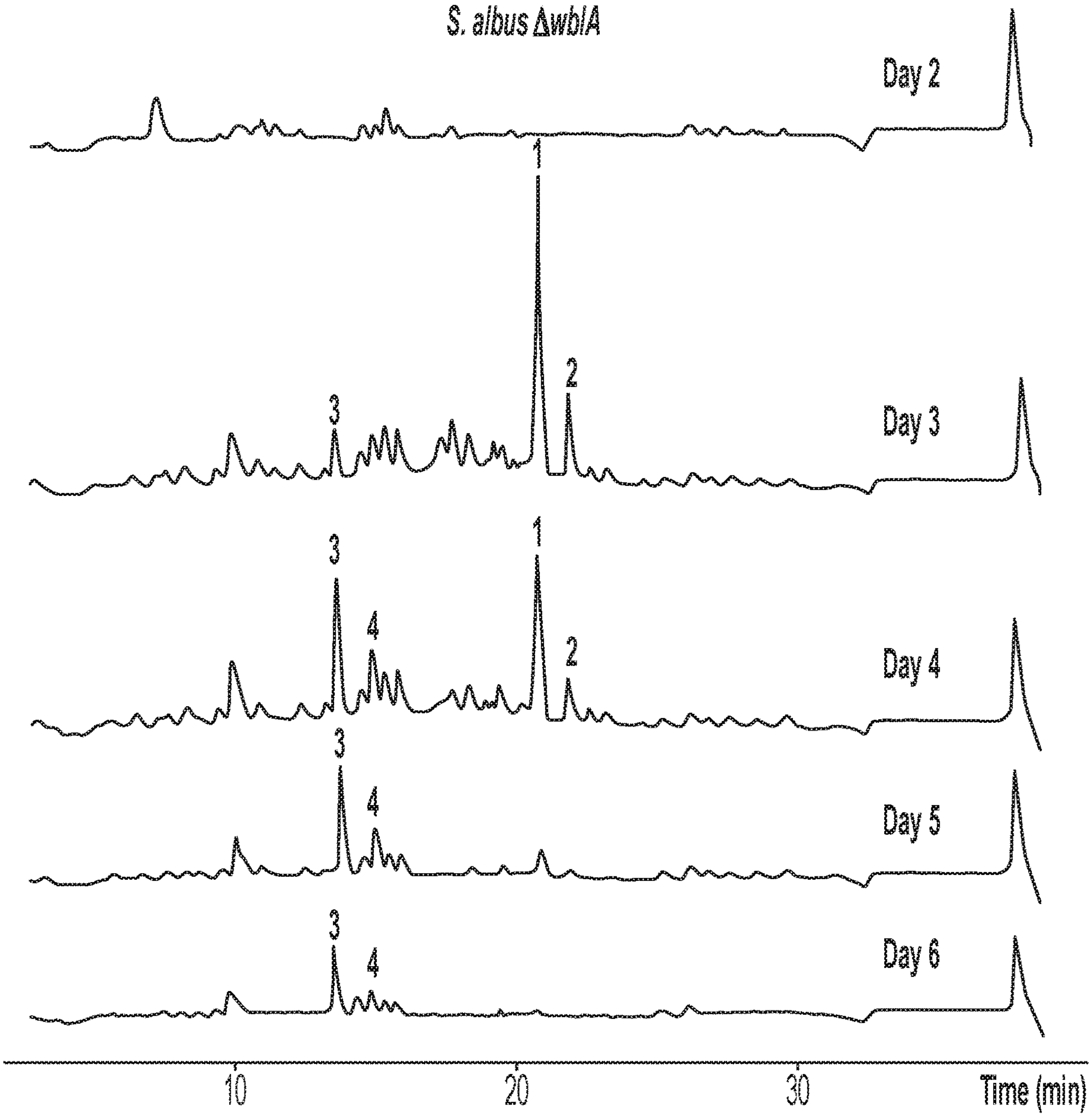
FIG. 9 shows LC-MS analysis of *S. albus* ΔwblA culture extracts collected daily for 6 days from R5A fermentation broths. 1, paulomycin B; 2, paulomycin A; 3, paulomenol B; 4, paulomenol A.
Figure 10:
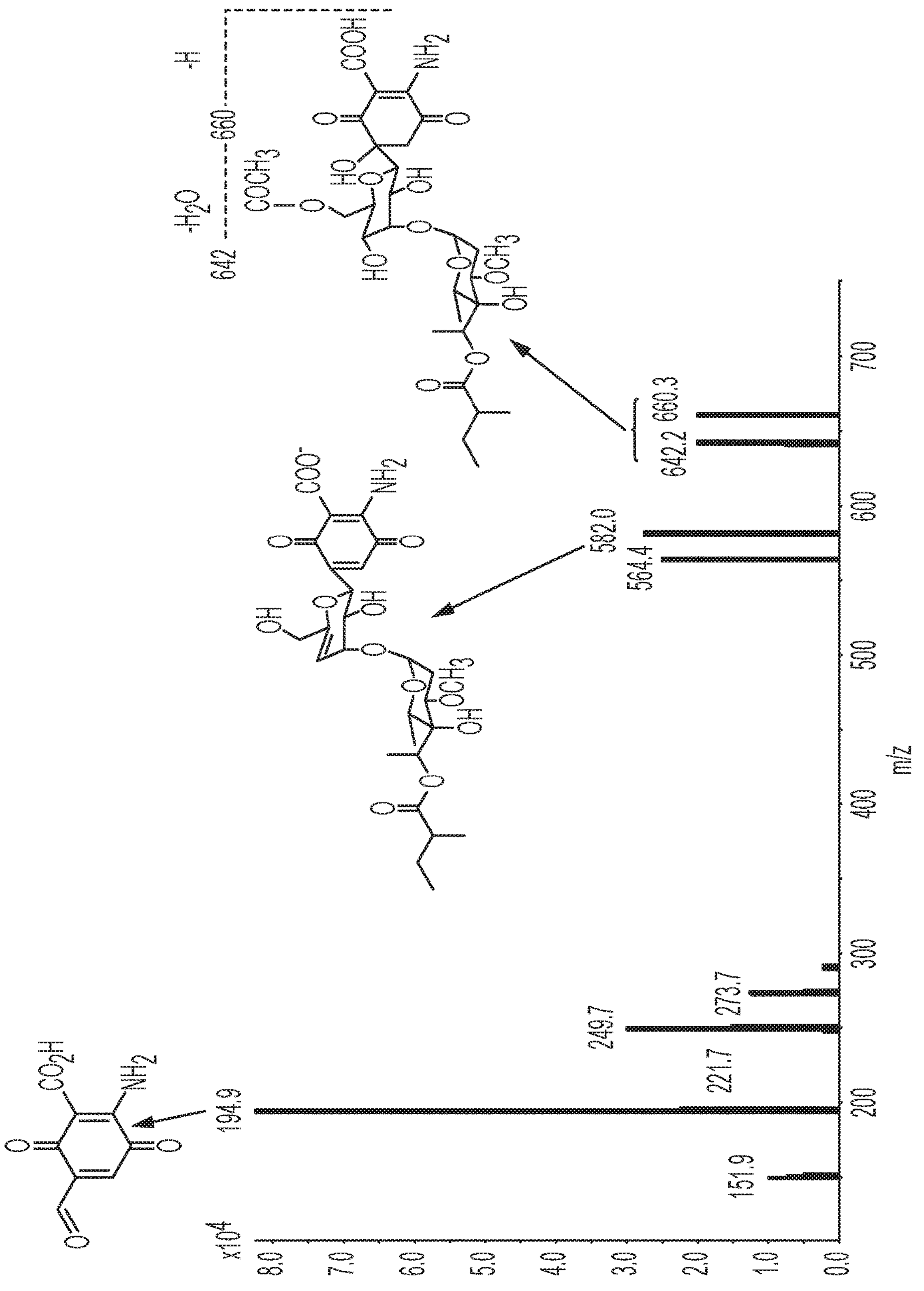
FIG. 10 shows an MS fragmentation pattern of paulomenol A. Negative mode.
Figure 11:
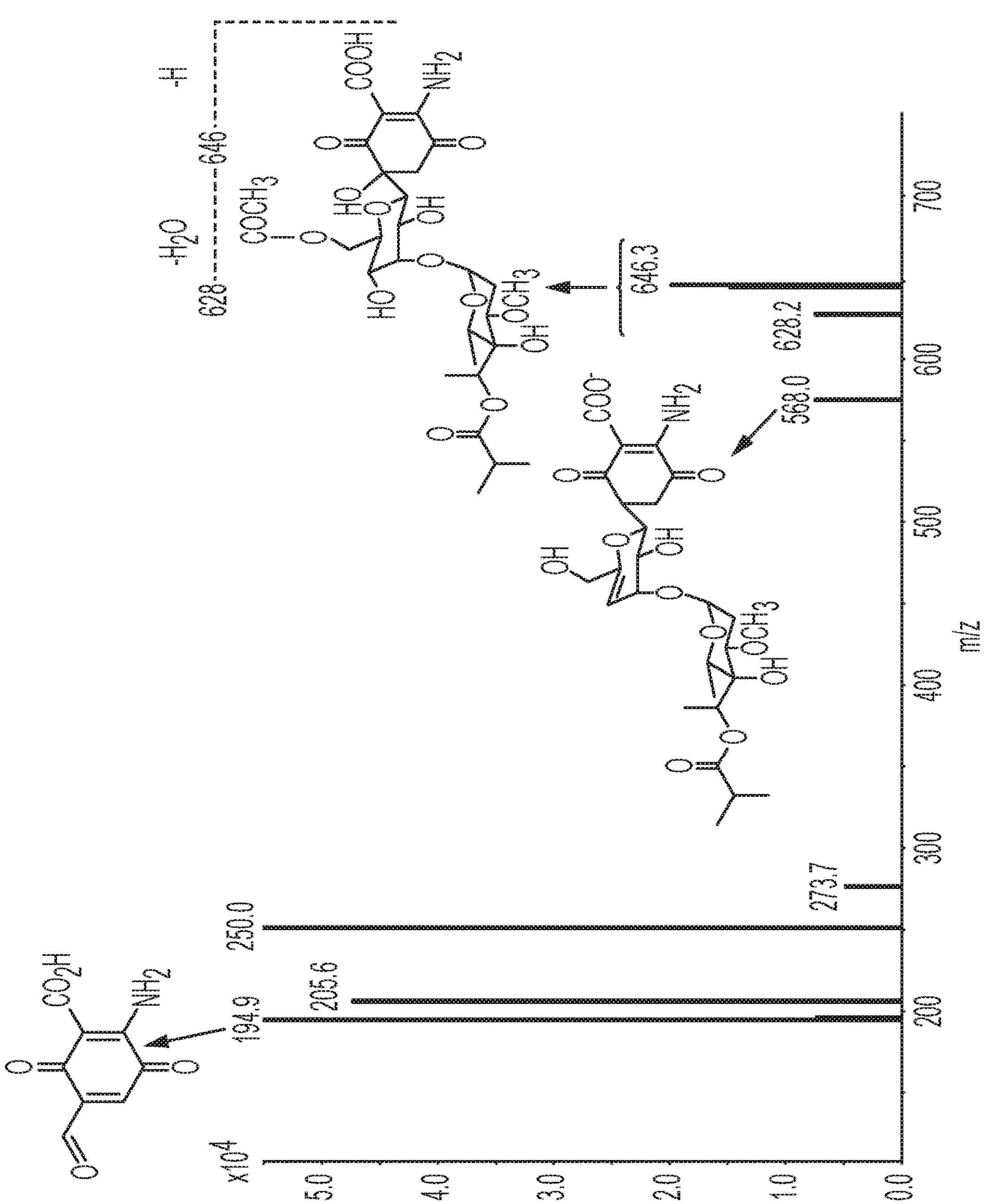
FIG. 11 shows an MS fragmentation pattern of paulomenol B. Negative mode.
Figure 12:
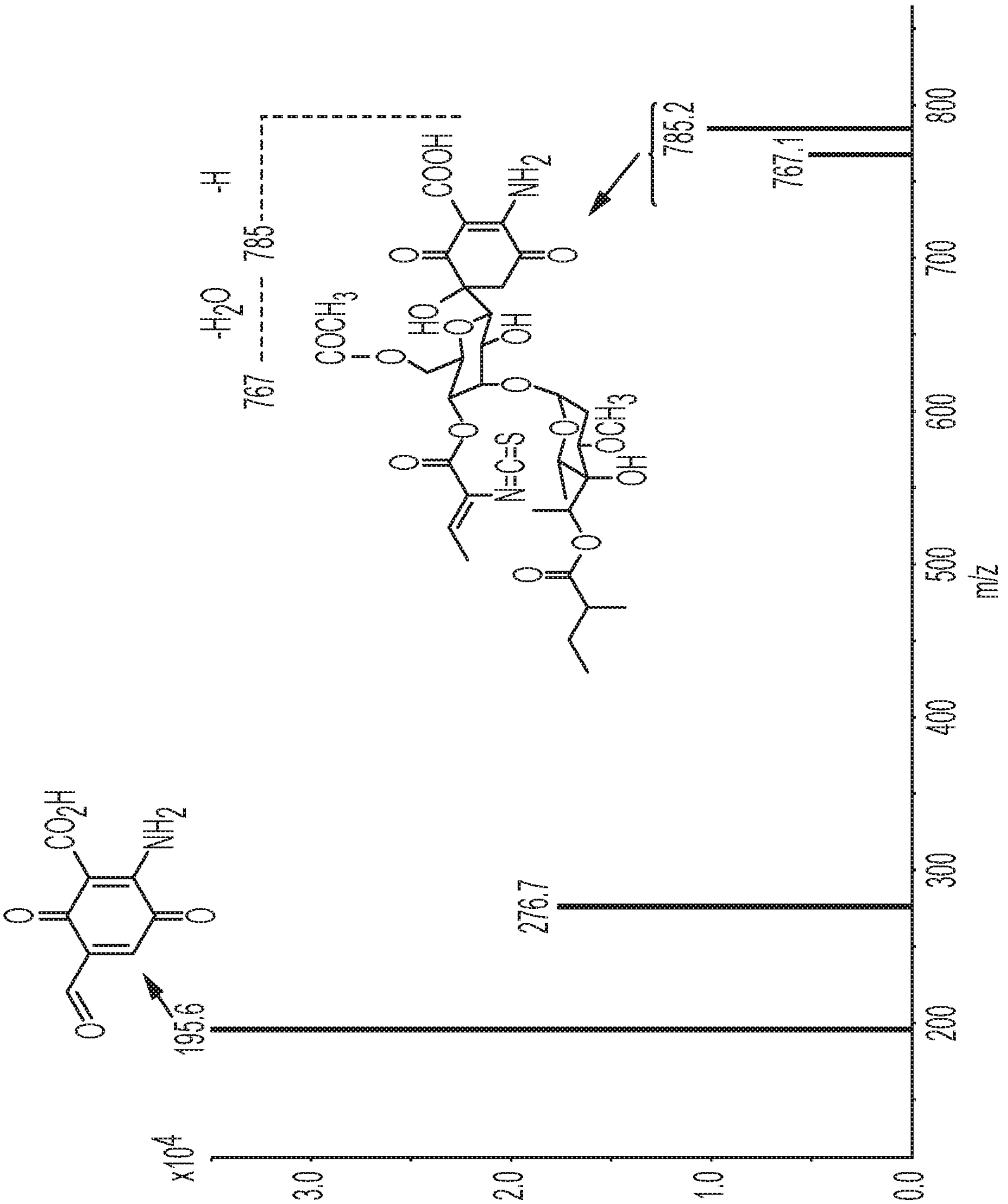
FIG. 12 shows an MS fragmentation pattern of paulomycin A. Negative mode.
Figure 13:
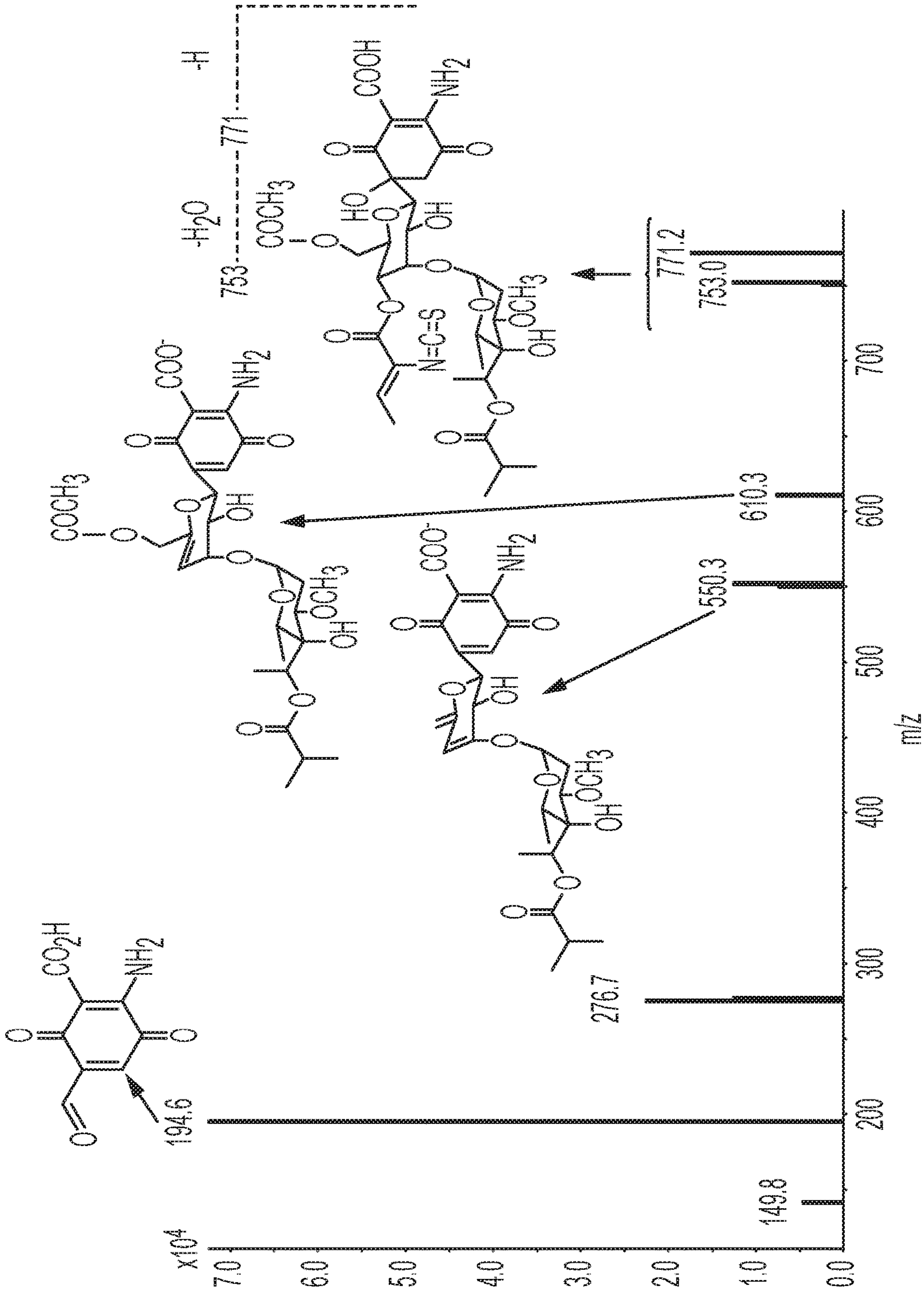
FIG. 13 shows an MS fragmentation pattern of paulomycin B. Negative mode.

Wild type and mutant strains of *S. albus* were grown in R5A media for 6 days and culture extracts were analyzed by LC-MS (FIG. 4A). Although the metabolic profile of Δpfk strain did not differ from that of wild type, ΔwblA and [+ermE*p-$crp_{SC}$] strains produced a set of metabolites that were absent in wild type extracts. The most dominant peaks (1-4) appeared at 13 min, 14 min, 20 min and 21 min. The [M+Na] masses of 670, 684, 795 and 809 respectively matched those of paulomenol B/A and paulomycin B/A, respectively. In addition compounds ½ and ¾ showed absorption spectra with maxima at 322 and 275 nm identical to paulomenols and paulomycin, respectively. In order to genetically verify the production of paulomenols/paulomycins in ΔwblA and [+ermE*$crp_{SC}$] strains, a 15-kb region was deleted from the paulomycin (plm) gene cluster that includes the pathway-specific regulator plm10 (FIGS. 5A-5B). These corresponding peaks disappeared from the culture extracts of resultant strains in LC-MS analysis (FIG. 5C and FIGS. 8-13). It is difficult to quantitate the production of paulomycins because of their partial degradation to paulomenols. Indeed the transition from paulomycin to paulomenols was observed when analyzing samples daily following inoculation from fermentation broths (FIG. 9). Nonetheless, based on the most dominant paulomenol B peak (peak #1) and the biomass produced by the engineered strains, there was a 2-fold increase in the production rate of the paulomenol B per mg dry biomass in [+ermE*$crp_{SC}$] background relative to ΔwblA mutation. Paulomycins differ from paulomenols by the presence of paulic acid that gives the characteristic UV absorption maxima at 275 nm and confers antimicrobial activity against Gram-positive bacteria. Extracts of ΔwblA and [+ermE*$crp_{SC}$] strains prepared after 4 days of growth in R5A media were active against *Bacillus cereus* (as low as 7.8 μg/ml) as opposed to extracts derived from wild type and Δplm backgrounds that showed no antimicrobial activity up to 500 μg/ml tested (FIG. 5D).

Using Regulatory Sequence Analysis Tools (RSAT; rsat.eu), the paulomycin gene cluster was scanned for possible CRP binding sites using the two reported sequence motifs, GTG(N)$_6$GNCAC (SEQ ID NO: 21) and the one with more relaxed binding specificity GTG(N)$_6$GNGAN (SEQ ID NO: 22). The first motif was found within the coding sequence of plm12, 28, 29, 35, 37 and plm40 genes while the second motif found within the coding sequences of plm2, 4, 6-10, 12, 23, 28, 32 and plm42 genes as well in the intergenic region plm7-plm8 genes (Table 2). Genes plm2 and plm 10 are two of the four transcriptional regulators found in the paulomycin cluster and specifically for plm2 gene putative CRP binding site starts five bases upstream of its start codon whereas overlaps the start codon of plm42 encoding for dTDP-4-keto-6-deoxyhexose 3,5-epimerase starting nine bases upstream of the corresponding start codon (Tables 2 and 3).

TABLE 2

Sequence scanning of paulomycin (plm) gene cluster for the detection of putative CRPSC binding sites using the GTG(N)$_6$GNCAC (SEQ ID NO: 21) motif. Distance from the beginning of the motif to the start codon of the corresponding genes is reported. Negative values indicate sites upstream of start codons while positive values indicate sites within open reading frames. SEQ ID NOs: 23-28 are shown, top to bottom.

| plm gene | Function | distance | Binding site, |
|---|---|---|---|
| plm 12 | Glycosyltransferase | +130 | cctcGTGGACACCGCCACcggc |
| plm 28 | Putative sulfotransferase | +628 | ggcgGTGGCCATGGCCACggag |
| plm 29 | Aminotransferase | +91 | cctgGTGCCGCTCGTCACcggc |
| plm 35 | Ribulose-5-phosphate-4-epimerase | +29 | acgcGTGAGCGAGGGCACcccg |
| plm 37 | Acyl-CoA dehydrogenase | +763 | cgcgGTGGGGCTCGCCACcgcg |
| plm 40 | dTDP-4-keto-6-deoxy-L-hexose 2,3-reductase | +301 | ccggGTGGTGCTGGCCACcaag |

TABLE 3

Sequence scanning of paulomycin (plm) gene cluster for the detection of putative CRPSC binding sites using the GTG(N)6GNGAN (SEQ ID NO: 22) motif. Distance from the beginning of the motif to the start codon of the corresponding genes is reported. Negative values indicate sites upstream of start codons while positive values indicate sites within open reading frames. SEQ ID NOs: 29-44 are shown, top to bottom.

| plm gene | Function | distance | Binding site |
|---|---|---|---|
| plm 2 | TetR-family transcriptional regulator | -5 | ggggGTGCGATGCGGGACgcgc |
| plm 4 | Oxidoreductase | +162 | ttcgGTGGGGACGGGGACacgg |
| plm 6 | EmrB/QacA subfamily transporter | +1230 | cagcGTGCCCGCCGCGACcacg |
| plm 7 | Elongation factor G1 | +1620 | gttcGTGAACAAGGTGACcggt |
| plm 8 | Dehydrogenase E1 alpha subunit | -299 | gggaGTGACCGACGCGACagcg |
| plm8 | Dehydrogenase E1 alpha subunit | +900 | gctgGTGGCGGAGGCGAGggac |
| plm 9 | Dehydrogenase E1 beta subunit | +333 | cggcGTGCCCGTGGTGACccgg |
| plm 9 | Dehydrogenase E1 beta subunit | +507 | ggtgGTGCTCATCGAGAAccgc |
| plm 9 | Dehydrogenase E1 beta subunit | +825 | cgcgGTGGTGGCCGAGAAcgta |
| plm 9 | Dehydrogenase E1 beta subunit | +864 | cccgGTGCGGCGGGTGACcctg |
| plm 10 | SARP-family transcriptional regulator | +153 | ccagGTGCTCCCGGCGACaacg |
| plm 12 | Glycosyltransferase | +672 | ggacGTGGCCGGGGAGACgctc |
| plm 23 | C-glycosyltransferase | +204 | gggcGTGCCCCTGGTGAGgtcc |
| plm 28 | Putative sulfotransferase | +390 | cctcGTGGTGTGCGCGAGcgag |
| plm 32 | Acyl-CoA synthase | +1221 | cgtgGTGCTCGAAGTGACcgac |
| plm 42 | dTDP-4-keto-6-deoxyhexose 3,5-epimerase | -9 | tgaaGTGGGGAGAGTGAGcccc |

Heterologous Expression of Actinorhodin in *S. albus* Engineered Strains

The effects of the gene-targeted engineering of *S. albus* genome on the expression of heterologous gene clusters was investigated. The model actinorhodin gene cluster, which encodes a diffusible pH-sensing pigment, was used in this example. A single fosmid harboring the gene cluster including flanking regions (SCO5067-SCO5104) was recovered from *S. coelicolor* M145 DNA library and retrofitted with oriT-integrase-apramycin cassette derived from pOJ436 vector. The resulting fosmid was transferred into *S. albus* mutant strains by intergeneric conjugation. The $wblA_{SA}$ sporulation-deficient phenotype was not ideal to function as a recipient strain in intergeneric conjugations for routine transfer of foreign gene clusters due to very low transfer rates when using mycelia fragments. Therefore, the heterologous expression assay was performed on the [ermE*$crp_{SC}$] single mutant and Δpfk+ermE*$crp_{SC}$ double mutant.

Figure 6:
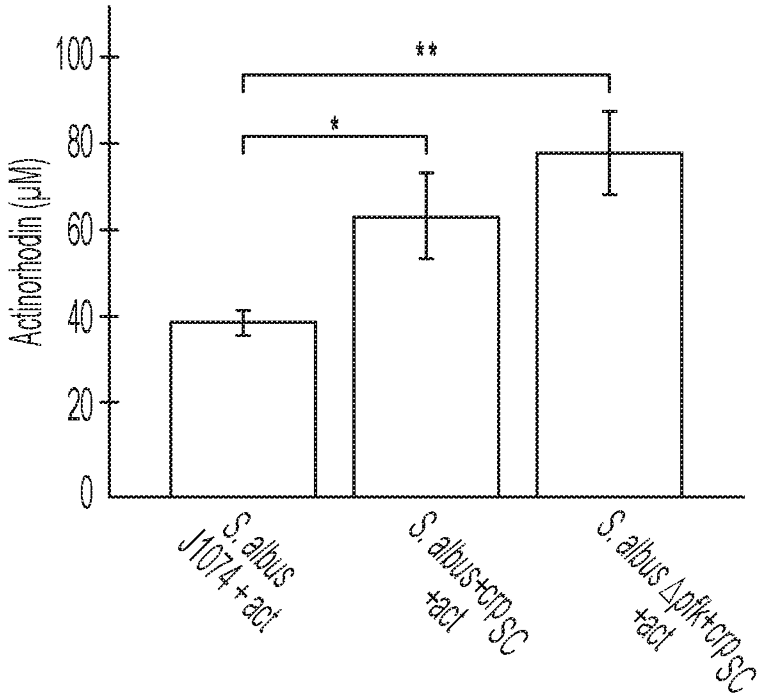
FIG. 6 shows quantification of heterologous expression of actinorhodin gene cluster in *S. albus* J1074 and derivative engineered strains. Synergistic effects of $crp_{SC}$ overexpression and $pfk_{SA}$ deletion on the actinorhodin production were observed. *S. albus*+ermE*$crp_{SC}$ increases the actinorhodin production by 1.6-fold and the double engineered *S. albus* Δpfk+ermE*$crp_{SC}$ strain by 2-fold relative to the *S. albus* J1074 (*$p<0.05$, **$p<0.01$.). Three different exconjugants from each strain were used in the experiment and values represent means of three biological replicates. Statistical significance was calculated with Student's t-test and one-way ANOVA from GraphPad Prism 6

Increased production of actinorhodin was observed that followed the corresponding sequentially accumulated gene modifications wt<[+ermE*$crp_{SC}$]<Δpfk+ermE*$crp_{SC}$ (FIG. 6). The transcriptional control of $crp_{SC}$ gene copy over actinorhodin gene cluster expression in *S. coelicolor* has been characterized. In the *S. albus* genetic context, overexpression of $crp_{SC}$ gene improved the heterologous expression of actinorhodin by 1.6-fold followed by an additional 1.2-fold when combined with the $pfk_{SA}$ deletion, indicating the approximately additive effect of these mutations to the actinorhodin biosynthesis.

Figure 7:
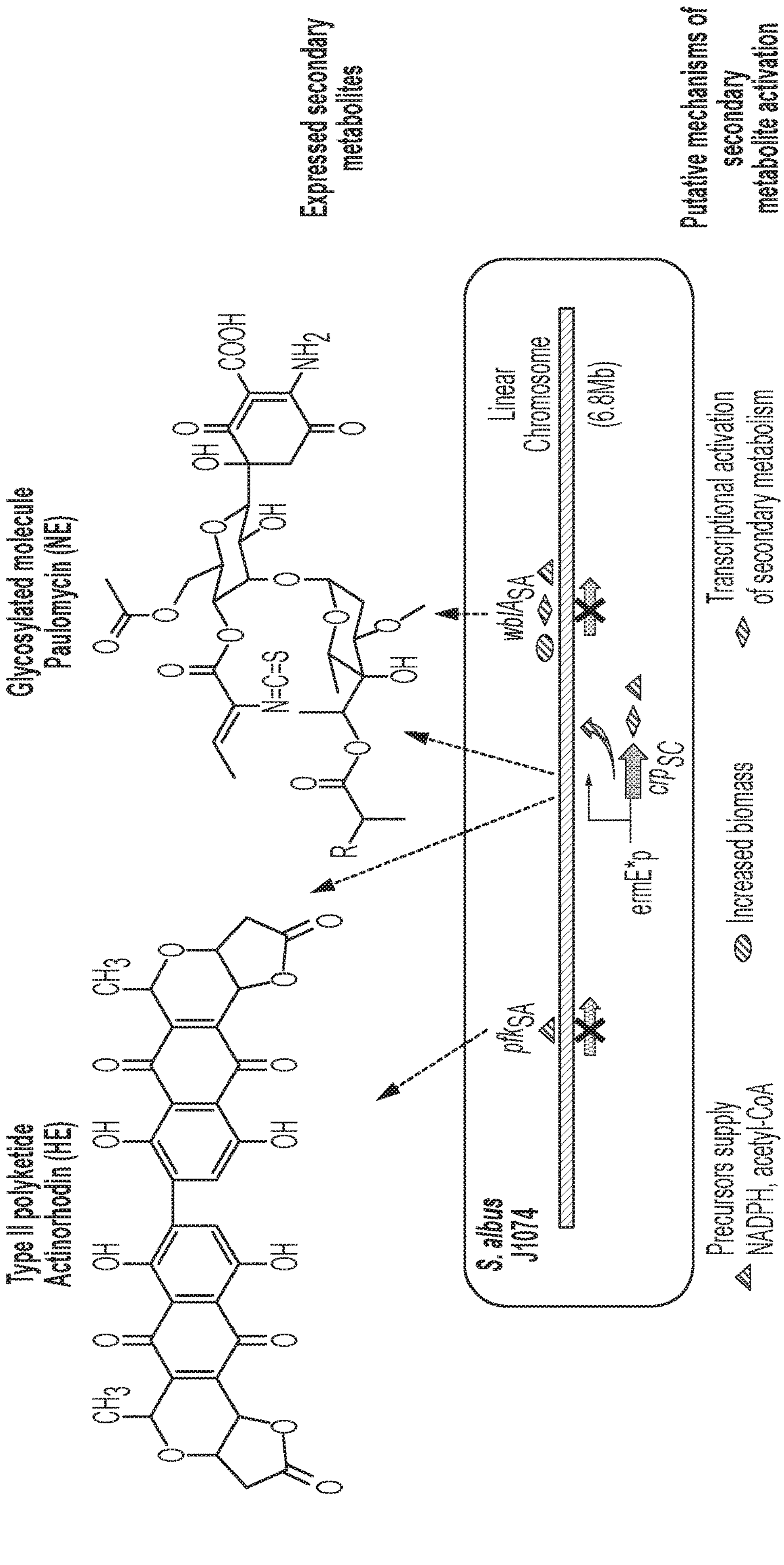
FIG. 7 is a schematic depicting one embodiment of a host engineering overview for *S. albus* J1074 strain improvement for expression of silent native biosynthetic pathways and the enhancement of the heterologous expression of foreign gene clusters. HE heterologous expression, NE native expression
Figure 8:
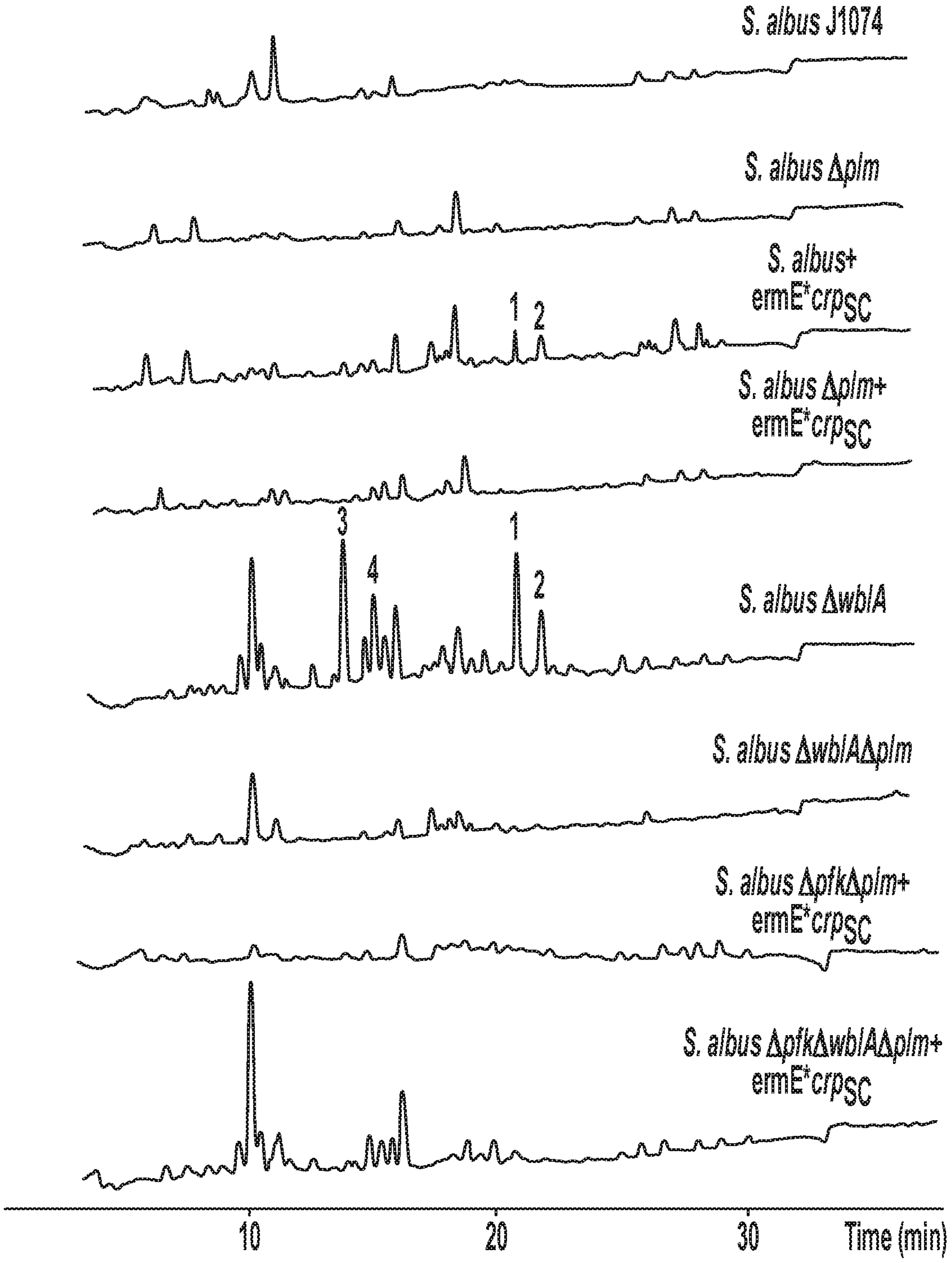
FIG. 8 shows confirmation of upregulation of paulomycin gene cluster (plm) by $crp_{SC}$ overexpression and $WblA_{SA}$ deletion by LC-MS analysis of organic extracts prepared from *Streptomyces albus* J1074 engineered strains grown in R5A media for 4 days. 1, paulomycin B; 2, paulomycin A; 3, paulomenol B; 4, paulomenol A.

Gene-targeted engineering of *S. albus* J1074 genome resulted in improved gene expression capabilities of secondary metabolism. Deletion of pfk gene supplied increased levels of NADPH reducing cofactor to the biosynthetic pathways containing NADPH-dependent enzymatic steps. Heterologous expression of actinorhodin was assisted by this genetic modification. Overexpression of the transcriptional regulator CRP from *S. coelicolor* in the *S. albus* background activated the expression of paulomycins, and functioned synergistically with global regulators controlling other modes of regulation of secondary metabolism like pfk for the heterologous expression of actinorhodin. Deletion of the global antibiotic down regulator WblA, induced the production of paulomycins in response to prolong fast growth and biomass accumulation. In sum, this example describes rational, multiplex genome engineering (FIG. 7) is an efficient way to unlock the expression of native metabolites and further enhance the heterologous expression properties of *S. albus* bacteria.

The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof.

What is claimed is:

1. A genetically engineered *Streptomyces* J1074 bacterium having a genotype selected from: +ermE*crpSCΔpfk, +ermE*crpSCΔwblAΔpfk, +ermE*crpSCΔpfkΔplm, and +ermE*crpSCΔwblAΔpfkΔplm.

2. A bacterial population comprising a plurality of the genetically engineered *Streptomyces* J1074 bacterium of claim 1.

3. A composition comprising a plurality of the genetically engineered *Streptomyces* J1074 bacterium of claim 1 and a bacterial culture medium.

4. The composition of claim 3, wherein the bacterial culture medium is a liquid medium.

5. The composition of claim 3, wherein the liquid medium comprises M9 medium, Lysogeny Broth (LB) medium, SOC medium, or Terrific Broth (TB).

* * * * *